US010806409B2

(12) United States Patent
Kruesi et al.

(10) Patent No.: US 10,806,409 B2
(45) Date of Patent: Oct. 20, 2020

(54) MEDICAL SYSTEMS WITH PATIENT SUPPORTS

(71) Applicant: VARIAN MEDICAL SYSTEMS INTERNATIONAL AG, Cham OT (CH)

(72) Inventors: Jonas Kruesi, Dietikon (CH); Niklaus Schaer, Dattwil (CH); Reto W. Filiberti, Steinhausen (CH); Joerg Blattner, Staefa (CH); Francois Besson, Illzach (FR)

(73) Assignee: Varian Medical Systems International AG (CH)

( * ) Notice: Subject to any disclaimer, the term of this patent is extended or adjusted under 35 U.S.C. 154(b) by 20 days.

(21) Appl. No.: 15/275,226

(22) Filed: Sep. 23, 2016

(65) Prior Publication Data
US 2018/0085603 A1    Mar. 29, 2018

(51) Int. Cl.
*A61B 6/04*    (2006.01)
*A61B 5/00*    (2006.01)
(Continued)

(52) U.S. Cl.
CPC .............. *A61B 6/04* (2013.01); *A61B 5/0555* (2013.01); *A61B 5/704* (2013.01); *A61B 6/0407* (2013.01); *A61B 6/0457* (2013.01); *A61B 6/4476* (2013.01); *A61N 5/10* (2013.01); *A61N 5/1039* (2013.01); *A61N 5/1049* (2013.01); *A61N 5/1078* (2013.01); *A61N 5/1081* (2013.01);
(Continued)

(58) Field of Classification Search
CPC ....... A61B 6/0457; A61B 6/04; A61B 6/0407; A61B 2034/306; A61B 2034/305; A61G 12/007; A61G 13/02; A61G 13/04; A61G 13/06; A61G 13/08; Y10T 74/20335
USPC ............................................................. 5/601
See application file for complete search history.

(56) References Cited

U.S. PATENT DOCUMENTS 3,133,227 A   5/1964 Brown et al.
3,144,552 A   8/1964 Schonberg et al.
(Continued)

FOREIGN PATENT DOCUMENTS

WO   WO 9927839   6/1999

OTHER PUBLICATIONS

International Search Report and Written Opinion dated Nov. 16, 2017 for corresponding PCT Patent Application No. PCT/EP2017/073821, 12 pages.

(Continued)

*Primary Examiner* — Kaylee R Wilson
(74) *Attorney, Agent, or Firm* — Vista IP Law Group, LLP

(57) ABSTRACT

A patient supporting device includes: a base configured to translate in a room; a first member having a first end and a second end, wherein the first end of the first member is rotatably coupled to the base so that the first member is rotatable relative to the base about a first vertical axis; a second member having a first end and a second end, wherein the first end of the second member is rotatably coupled to the second end of the first member so that the second member is rotatable relative to the first member about a second vertical axis; and a platform for supporting a patient, wherein the platform is rotatably coupled to the second end of the second member so that the platform is rotatable relative to the second member about a third vertical axis.

55 Claims, 12 Drawing Sheets

(51) Int. Cl.
 *A61N 5/10* (2006.01)
 *A61B 5/055* (2006.01)
 *A61B 6/00* (2006.01)
 *A61B 6/03* (2006.01)

(52) U.S. Cl.
 CPC ............. *A61B 6/035* (2013.01); *A61B 6/4429* (2013.01); *A61N 2005/1052* (2013.01); *A61N 2005/1055* (2013.01); *A61N 2005/1058* (2013.01); *A61N 2005/1059* (2013.01); *A61N 2005/1061* (2013.01); *A61N 2005/1087* (2013.01)

(56) References Cited

U.S. PATENT DOCUMENTS

| | | |
|---|---|---|
| 3,193,717 A | 7/1965 | Nunan |
| 3,504,179 A | 3/1970 | Hainault |
| 3,751,028 A | 8/1973 | Scheininger et al. |
| 3,837,635 A | 9/1974 | Long et al. |
| 3,843,112 A | 10/1974 | McDonald |
| 3,948,559 A | 4/1976 | Hain et al. |
| 3,987,281 A | 10/1976 | Hodes |
| 4,112,306 A | 9/1978 | Nunan |
| 4,149,247 A | 4/1979 | Pavkovich et al. |
| 4,149,248 A | 4/1979 | Pavkovich |
| 4,208,675 A | 6/1980 | Bajon et al. |
| 4,209,706 A | 6/1980 | Nunan |
| 4,314,158 A | 2/1982 | Lucido |
| 4,521,808 A | 6/1985 | Ong et al. |
| 4,542,547 A | 9/1985 | Sato |
| 4,547,892 A | 10/1985 | Richey et al. |
| 4,589,126 A | 5/1986 | Augustsson et al. |
| 4,593,967 A | 6/1986 | Haugen |
| 4,628,523 A | 12/1986 | Heflin |
| 4,675,731 A | 6/1987 | Takasu et al. |
| 4,679,076 A | 7/1987 | Vikterlof et al. |
| 4,726,046 A | 2/1988 | Nunan |
| 4,741,621 A | 5/1988 | Taft et al. |
| 4,825,393 A | 4/1989 | Nishiya |
| 4,853,777 A | 8/1989 | Hupp |
| 4,868,843 A | 9/1989 | Nunan |
| 4,868,844 A | 9/1989 | Nunan |
| 4,894,855 A | 1/1990 | Kresse |
| 4,924,781 A | 5/1990 | Span |
| 4,949,408 A | 8/1990 | Trkla |
| 5,001,344 A | 3/1991 | Kato et al. |
| 5,013,018 A | 5/1991 | Sicek et al. |
| 5,014,292 A | 5/1991 | Siczek et al. |
| 5,027,818 A | 5/1991 | Bova et al. |
| 5,039,867 A | 8/1991 | Nishihara et al. |
| 5,044,354 A | 9/1991 | Goldhorn et al. |
| 5,080,100 A | 1/1992 | Trotel |
| 5,099,505 A | 3/1992 | Seppi et al. |
| 5,117,445 A | 5/1992 | Seppi et al. |
| 5,117,829 A | 5/1992 | Miller et al. |
| 5,157,707 A | 10/1992 | Ohlson |
| 5,168,532 A | 12/1992 | Seppi et al. |
| 5,207,223 A | 5/1993 | Adler |
| 5,233,990 A | 8/1993 | Barnea |
| 5,247,555 A | 9/1993 | Moore et al. |
| 5,262,649 A | 11/1993 | Antonuk et al. |
| 5,317,616 A | 5/1994 | Swerdloff et al. |
| 5,329,567 A | 7/1994 | Ikebe |
| 5,332,908 A | 7/1994 | Weidlich |
| 5,335,255 A | 8/1994 | Seppi et al. |
| 5,379,468 A | 1/1995 | Cassidy et al. |
| 5,394,452 A | 2/1995 | Swerdloff et al. |
| 5,400,255 A | 3/1995 | Hu |
| 5,410,767 A * | 5/1995 | Barud .................. A61B 6/04 108/143 |
| 5,411,026 A | 5/1995 | Carol |
| 5,427,097 A | 6/1995 | Depp |
| 5,438,991 A | 8/1995 | Yu et al. |
| 5,442,675 A | 8/1995 | Swerdloff et al. |
| 5,471,516 A | 11/1995 | Nunan |
| 5,471,546 A | 11/1995 | Meier |
| 5,509,042 A | 4/1996 | Mazess |
| 5,521,957 A | 5/1996 | Hansen |
| 5,525,905 A | 6/1996 | Mohapatra et al. |
| 5,528,650 A | 6/1996 | Swerdloff et al. |
| 5,533,082 A | 7/1996 | Gronemeyer et al. |
| 5,537,452 A | 7/1996 | Shepherd et al. |
| 5,548,627 A | 8/1996 | Swerdloff et al. |
| 5,552,606 A | 9/1996 | Jones et al. |
| 5,591,983 A | 1/1997 | Yao |
| 5,615,430 A | 4/1997 | Nambu et al. |
| 5,625,663 A | 4/1997 | Swerdloff et al. |
| 5,647,663 A | 7/1997 | Holmes |
| 5,651,043 A | 7/1997 | Tsuyuki et al. |
| 5,661,773 A | 8/1997 | Swerdloff et al. |
| 5,663,995 A | 9/1997 | Hu |
| 5,663,999 A | 9/1997 | Siochi |
| 5,673,300 A | 9/1997 | Reckwerdt et al. |
| 5,675,625 A | 10/1997 | Rockseisen |
| 5,681,326 A | 10/1997 | Lax |
| 5,692,507 A | 12/1997 | Seppi et al. |
| 5,719,914 A | 2/1998 | Rand et al. |
| 5,724,400 A | 3/1998 | Swerdloff et al. |
| 5,748,700 A | 5/1998 | Shepherd et al. |
| 5,748,703 A | 5/1998 | Cosman |
| 5,748,907 A | 5/1998 | Crane |
| 5,751,781 A | 5/1998 | Brown et al. |
| 5,757,881 A | 5/1998 | Hughes |
| 5,802,136 A | 9/1998 | Carol |
| 5,818,902 A | 10/1998 | Yu |
| 5,835,558 A | 11/1998 | Maschke |
| 5,842,987 A | 12/1998 | Sahadevan |
| 5,848,126 A | 12/1998 | Fujita et al. |
| 5,851,182 A | 12/1998 | Sahadevan |
| 5,859,891 A | 1/1999 | Hibbard |
| 5,877,501 A | 3/1999 | Ivan et al. |
| 5,912,943 A | 6/1999 | Deucher et al. |
| 5,926,521 A | 7/1999 | Tam |
| 5,929,449 A | 7/1999 | Huang |
| 5,949,811 A | 9/1999 | Baba et al. |
| 5,956,382 A | 9/1999 | Wiener-Avnear et al. |
| 5,960,055 A | 9/1999 | Samarasekera et al. |
| 5,999,587 A | 12/1999 | Ning et al. |
| 6,031,888 A | 2/2000 | Ivan et al. |
| 6,038,283 A | 3/2000 | Carol et al. |
| 6,041,097 A | 3/2000 | Roos et al. |
| 6,052,430 A | 4/2000 | Siochi et al. |
| 6,075,836 A | 6/2000 | Ning |
| 6,078,638 A | 6/2000 | Sauer et al. |
| 6,094,760 A * | 8/2000 | Nonaka .................. A61B 6/0457 5/600 |
| 6,104,778 A | 8/2000 | Murad |
| 6,104,780 A | 8/2000 | Hanover et al. |
| 6,108,400 A | 8/2000 | Siochi |
| 6,113,264 A | 9/2000 | Watanabe |
| 6,134,296 A | 10/2000 | Siochi |
| 6,142,925 A | 11/2000 | Siochi et al. |
| 6,144,875 A | 11/2000 | Schweikard et al. |
| 6,148,058 A | 11/2000 | Dobbs |
| 6,152,598 A | 11/2000 | Tomisaki et al. |
| 6,170,102 B1 | 1/2001 | Kreuzer |
| 6,200,024 B1 | 3/2001 | Negrelli |
| 6,219,403 B1 | 4/2001 | Nishihara |
| 6,219,441 B1 | 4/2001 | Hu |
| 6,222,901 B1 | 4/2001 | Meulenbrugge et al. |
| 6,240,161 B1 | 5/2001 | Siochi |
| 6,260,005 B1 | 7/2001 | Yang et al. |
| 6,269,141 B1 | 7/2001 | Proksa et al. |
| 6,269,143 B1 | 7/2001 | Tachibana |
| 6,278,766 B1 | 8/2001 | Kooy et al. |
| 6,285,739 B1 | 9/2001 | Rudin et al. |
| 6,292,526 B1 | 9/2001 | Patch |
| 6,307,914 B1 | 10/2001 | Kunieda et al. |
| 6,314,159 B1 | 11/2001 | Siochi |
| 6,318,892 B1 | 11/2001 | Suzuki et al. |
| 6,325,537 B1 | 12/2001 | Watanabe |
| 6,325,758 B1 | 12/2001 | Carol et al. |
| 6,330,300 B1 | 12/2001 | Siochi |

(56) References Cited

U.S. PATENT DOCUMENTS

| | | |
|---|---|---|
| 6,335,961 B1 | 1/2002 | Wofford et al. |
| 6,345,114 B1 | 2/2002 | Mackie et al. |
| 6,349,129 B1 | 2/2002 | Siochi |
| 6,353,222 B1 | 3/2002 | Dotan |
| 6,370,421 B1 | 4/2002 | Williams et al. |
| 6,381,302 B1 | 4/2002 | Berestov |
| 6,385,286 B1 | 5/2002 | Fitchard et al. |
| 6,385,288 B1 | 5/2002 | Kanematsu |
| 6,385,477 B1 | 5/2002 | Werner et al. |
| 6,393,096 B1 | 5/2002 | Carol et al. |
| 6,405,072 B1 | 6/2002 | Cosman |
| 6,411,675 B1 | 6/2002 | Llacer |
| 6,429,578 B1 | 8/2002 | Danielsson et al. |
| 6,435,715 B1 | 8/2002 | Betz et al. |
| 6,438,202 B1 | 8/2002 | Olivera et al. |
| 6,445,766 B1 | 9/2002 | Whitham |
| 6,463,122 B1 | 10/2002 | Moore |
| 6,473,490 B1 | 10/2002 | Siochi |
| 6,480,565 B1 | 11/2002 | Ning |
| 6,490,476 B1 | 12/2002 | Townsend et al. |
| 6,502,261 B1 | 1/2003 | Hardwood |
| 6,504,892 B1 | 1/2003 | Ning |
| 6,508,586 B2 | 1/2003 | Oota |
| 6,560,311 B1 | 5/2003 | Shepard et al. |
| 6,590,953 B2 | 7/2003 | Suzuki et al. |
| 6,611,700 B1 | 8/2003 | Vilsmeier et al. |
| 6,618,467 B1 | 9/2003 | Ruchaia et al. |
| 6,621,889 B1 | 9/2003 | Mostafavi |
| 6,640,364 B1 | 11/2003 | Josephson et al. |
| 6,661,870 B2 | 12/2003 | Kapatoes et al. |
| 6,665,554 B1 | 12/2003 | Charles et al. |
| 6,710,557 B1 | 3/2004 | Allen et al. |
| 6,735,277 B2 | 5/2004 | McNutt et al. |
| 6,744,848 B2 | 6/2004 | Stanton et al. |
| 6,769,806 B2 | 8/2004 | Moyers |
| 6,800,858 B1 | 10/2004 | Seppi |
| 6,841,782 B1 | 1/2005 | Balan et al. |
| 6,842,502 B2 | 1/2005 | Jaffray et al. |
| 6,865,254 B2 | 3/2005 | Nafstadius |
| 6,888,919 B2 | 5/2005 | Graf |
| 6,914,959 B2 | 7/2005 | Bailey et al. |
| 6,959,266 B1 | 10/2005 | Mostafavi |
| 6,973,202 B2 | 12/2005 | Mostafavi |
| 6,980,679 B2 | 12/2005 | Jeung |
| 7,008,105 B2 | 3/2006 | Amann et al. |
| 7,054,410 B2 | 5/2006 | Zenta |
| 7,095,028 B2 | 8/2006 | Molloy |
| 7,251,845 B2 | 8/2007 | Schaller et al. |
| 7,328,055 B2 | 2/2008 | Bonutti |
| 7,471,765 B2 | 12/2008 | Jaffray et al. |
| 7,603,164 B2 | 10/2009 | Uematsu |
| 7,640,607 B2 | 1/2010 | Guertin et al. |
| 7,649,981 B2 | 1/2010 | Seppi et al. |
| 7,826,592 B2 | 11/2010 | Jaffray et al. |
| 7,945,021 B2 | 5/2011 | Shapiro et al. |
| 8,116,430 B1 | 2/2012 | Shapiro et al. |
| 8,135,111 B2 | 3/2012 | Jaffray et al. |
| 8,160,205 B2 | 4/2012 | Saracen et al. |
| 8,740,880 B2 | 6/2014 | Pinault et al. |
| 8,867,703 B2 | 10/2014 | Shapiro et al. |
| 2001/0001807 A1 | 5/2001 | Green |
| 2001/0008271 A1 | 7/2001 | Ikeda et al. |
| 2002/0006182 A1 | 1/2002 | Kim et al. |
| 2002/0066860 A1 | 6/2002 | Possin |
| 2002/0077749 A1 | 6/2002 | Doi |
| 2002/0080912 A1 | 6/2002 | Mackie et al. |
| 2002/0130279 A1 | 9/2002 | Jain et al. |
| 2002/0151786 A1 | 10/2002 | Shukla |
| 2002/0179812 A1 | 12/2002 | Kochi et al. |
| 2002/0191734 A1 | 12/2002 | Kojima et al. |
| 2002/0193685 A1 | 12/2002 | Mate et al. |
| 2003/0007601 A1 | 1/2003 | Jaffray et al. |
| 2003/0048868 A1 | 3/2003 | Bailey et al. |
| 2004/0024300 A1 | 2/2004 | Graf |
| 2004/0030246 A1 | 2/2004 | Townsend et al. |
| 2004/0034438 A1 | 2/2004 | Uematsu |
| 2004/0057557 A1 | 3/2004 | Nafstadius |
| 2004/0167398 A1 | 8/2004 | Flohr et al. |
| 2004/0210126 A1 | 10/2004 | Hajaj et al. |
| 2004/0220467 A1 | 11/2004 | Bonutti |
| 2004/0254773 A1 | 12/2004 | Zhang et al. |
| 2004/0260176 A1 | 12/2004 | Wollenweber et al. |
| 2005/0053267 A1 | 3/2005 | Mostafavi |
| 2005/0054916 A1 | 3/2005 | Mostafavi |
| 2005/0080332 A1 | 4/2005 | Shiu et al. |
| 2005/0082491 A1 | 4/2005 | Seppi |
| 2005/0084073 A1 | 4/2005 | Seppi et al. |
| 2005/0138732 A1 | 6/2005 | Erbel et al. |
| 2005/0197564 A1 | 9/2005 | Dempsey |
| 2005/0234327 A1 | 10/2005 | Saracen et al. |
| 2006/0113482 A1 | 6/2006 | Pelizzari et al. |
| 2006/0118736 A1 | 6/2006 | Moriyama et al. |
| 2007/0003021 A1 | 1/2007 | Guertin et al. |
| 2009/0070936 A1* | 3/2009 | Henderson ........... A61B 6/0457 5/601 |
| 2011/0066278 A1 | 3/2011 | Pinault et al. |
| 2013/0025055 A1 | 1/2013 | Saracen et al. |
| 2014/0033432 A1* | 2/2014 | Marle ................. A61G 7/1057 5/601 |
| 2014/0105355 A1* | 4/2014 | Toimela ................ A61N 5/103 378/41 |
| 2016/0067525 A1* | 3/2016 | Bouchet ............... A61N 5/1049 600/1 |
| 2018/0289574 A1* | 10/2018 | Hiratsuka ................ A61N 5/10 |

OTHER PUBLICATIONS

Non-final Office Action dated Sep. 18, 2008 for related U.S. Appl. No. 11/415,974.
Final Office Action dated May 8, 2009 for related U.S. Appl. No. 11/415,974.
Advisory Action dated Jul. 23, 2009 for related U.S. Appl. No. 11/415,974.
Notice of Allowance and Fee(s) due dated Aug. 24, 2009 for related U.S. Appl. No. 11/415,974.
Gerald Silke, et al., "An advanced Six Axis Patient Positioner for Use in Proton Therapy" Proceedings of the ANS Seventh Topical Meeting on Robotics and Remote Systems, vol. 1, Apr. 27 to May 1, 1997, 6 pages.
MaAdmin, MedAustron, "Neue Technik Ermoglicht Nie Da Gewesene Prazision in Der Krebsb", May, 8, 2015, 2 pages.
Hepha medical, Passion for Medical Robotics Research, "Welcome to the HEPHA advanced technology", Sep. 24, 2010, 10 pages.
Hepha Vulcain, Jan. 11, 2011, 1 page.
Hepha Eagle, Jan. 11, 2011, 1 page.
Final Office Action dated Oct. 26, 2018 for U.S. Appl. No. 15/467,930, 13 pages.
Non-Final Office Action dated Jul. 21, 2009 for U.S. Appl. No. 11/415,866.
Non-Final Office Action dated Feb. 3, 2009 for U.S. Appl. No. 11/415,866.
Final Office Action dated Jan. 11, 2010 for U.S. Appl. No. 11/415,866.
Non-Final Office Action dated Jun. 21, 2010 for U.S. Appl. No. 11/415,866.
Office Action dated Dec. 7, 2010 for U.S. Appl. No. 11/415,866.
Notice of Allowance dated Feb. 17, 2011 for U.S. Appl. No. 11/415,866.
Non-Final Office Action dated Aug. 6, 2008 for U.S. Appl. No. 11/415,965.
Final Office Action dated Feb. 5, 2009 for U.S. Appl. No. 11/415,965.
Advisory Action dated Jul. 10, 2009 for U.S. Appl. No. 11/415,965.
Advisory Action dated May 28, 2009 for U.S. Appl. No. 11/415,965.
Non-Final Office Action dated Apr. 2, 2010 for U.S. Appl. No. 11/415,957.
Final Office Action dated Sep. 15, 2010 for U.S. Appl. No. 11/415,957.
Non-Final Office Action dated Apr. 5, 2011 for U.S. Appl. No. 11/415,957.
Final Office Action dated Nov. 1, 2010 for U.S. Appl. No. 11/415,957.

(56) References Cited

OTHER PUBLICATIONS

Non-Final Office Action dated Feb. 28, 2012 for U.S. Appl. No. 11/415,957.
U.S. Appl. No. 10/454,754, filed Jun. 3, 2003 Titled Method and System for Predictive Physiological Gating of Radiation Therapy.
Final Office Action dated Jul. 11, 2012 for U.S. Appl. No. 11/415,957.
Advisory Action dated Sep. 27, 2012 for U.S. Appl. No. 11/415,957.
Non-final Office Action dated Nov. 6, 2012, for U.S. Appl. No. 13/164,698.
Final Office Action dated May 22, 2013, for U.S. Appl. No. 13/164,698.
Non-final Office Action dated Dec. 3, 2013, for U.S. Appl. No. 13/164,698.
Final Office Action dated Jul. 9, 2014, for U.S. Appl. No. 13/164,698.
Advisory Action dated Oct. 3, 2014 for U.S. Appl. No. 13/164,698.
Non-final Office Action dated Feb. 9, 2015 for U.S. Appl. No. 13/164,698.
Final Office Action dated Sep. 24, 2015 for related U.S. Appl. No. 13/164,698.
Advisory Action dated Dec. 10, 2015 for related U.S. Appl. No. 13/164,698.
Non-final Office Action dated Feb. 29, 2016 for related U.S. Appl. No. 13/164,698.
Notice of Allowance and Fee(s) due dated Apr. 5, 2016 for related U.S. Appl. No. 11/415,957.
Non-final Office Action dated Sep. 8, 2016 for related U.S. Appl. No. 13/164,698.
Non-final Office Action dated Feb. 9, 2017 for related U.S. Appl. No. 15/188,864.
Final Office Action dated Apr. 17, 2017 for related U.S. Appl. No. 13/164,698.
Final Office Action dated Jun. 15, 2017 for related U.S. Appl. No. 15/188,864.
Advisory Action dated Jul. 10, 2017 for related U.S. Appl. No. 13/164,698.
Non-final Office Action dated Jul. 21, 2017 for related U.S. Appl. No. 13/164,698.
Advisory Action dated Aug. 28, 2017 for related U.S. Appl. No. 15/188,864.
Non-final Office Action dated Sep. 11, 2017 for related U.S. Appl. No. 15/188,864.
Notice of Allowance dated Feb. 5, 2018 for related U.S. Appl. No. 15/188,864.
Final Office Action dated Feb. 5, 2018 for U.S. Appl. No. 13/164,698.
Advisory Action dated Apr. 20, 2018 for U.S. Appl. No. 13/164,698.
Non-Final Office Action dated Apr. 23, 2018 for U.S. Appl. No. 15/467,930.
Notice of Allowance dated Sep. 11, 2018 for U.S. Appl. No. 13/164,698.

\* cited by examiner

MEDICAL SYSTEMS WITH PATIENT SUPPORTS

FIELD

This application relates generally to medical systems, and more specifically, to medical systems with patient supports.

BACKGROUND

Radiation therapy has been employed to treat tumorous tissue. In radiation therapy, a high energy beam is applied from an external source towards the patient. The external source, which may be rotating (as in the case for arc therapy), produces a collimated beam of radiation that is directed into the patient to the target site. The dose and placement of the dose must be accurately controlled to ensure that the tumor receives sufficient radiation, and that damage to the surrounding healthy tissue is minimized.

Sometimes, in a radiation treatment procedure, a plurality of treatment sessions may be performed. In each treatment session, a radiation source may be placed at various prescribed gantry angles to thereby deliver radiation beam towards a target tissue from different angles. As a result of delivering radiation towards the target tissue from a plurality of different angles, a sufficient radiation dose may be delivered to the target tissue to thereby treat the target tissue, while surrounding healthy tissue may be protected.

Methods and apparatuses for positioning a patient relative to a treatment machines are described herein.

SUMMARY

A patient supporting device includes: a base configured to translate in a room; a first member having a first end and a second end, wherein the first end of the first member is rotatably coupled to the base so that the first member is rotatable relative to the base about a first vertical axis; a second member having a first end and a second end, wherein the first end of the second member is rotatably coupled to the second end of the first member so that the second member is rotatable relative to the first member about a second vertical axis; and a platform for supporting a patient, wherein the platform is rotatably coupled to the second end of the second member so that the platform is rotatable relative to the second member about a third vertical axis.

Optionally, the second member comprises a first member portion and a second member portion, the first member portion comprising the first end of the second member, the second member portion comprising the second end of the second member, wherein the second member portion is rotatably coupled to the first member portion so that the second member portion is rotatable relative to the first member portion about a first horizontal axis.

Optionally, the platform is rotatably coupled to the second member portion so that the platform is rotatable relative to the second member portion about a second horizontal axis.

Optionally, a rotation of the platform relative to the second member portion about the second horizontal axis, and a rotation of the second member portion relative to the first member portion about the first horizontal axis, are synchronized to move the platform vertically.

Optionally, the base is configured to move along a first rail.

Optionally, the first rail has a rectilinear configuration.

Optionally, the base is also configured to move along a second rail that is parallel to the first rail.

Optionally, the first member comprises a first arm, and the second member comprises a second arm.

Optionally, the platform comprises a longitudinal axis, and the platform is configured to tilt about the longitudinal axis.

Optionally, the platform is rotatably coupled to the second member portion of the second member, so that the platform is rotatable relative to the second member portion about an axis in longitudinal direction of the second member portion of the second member, or about a longitudinal axis of the platform.

Optionally, the patient supporting device further includes one or more cameras coupled to the platform.

Optionally, the one or more cameras comprises an optical camera, a depth camera, or both.

Optionally, the platform is detachably coupled to a remaining part of the patient supporting device.

Optionally, the patient supporting device further includes a control for allowing an operator to enter one or more commands to control a positioning and/or movement of the platform.

Optionally, the patient supporting device further includes one or more positional indicators.

Optionally, the one or more positional indicators comprise one or more markers at the platform, one or more markers at the first member, one or more markers at the second members, one or more markers at the base, or any combination of the foregoing.

Optionally, the one or more positional indicators comprise one or more beacons at the platform, one or more beacons at the first member, one or more beacons at the second members, one or more beacons at the base, or any combination of the foregoing.

Optionally, the one or more positional indicators comprise one or more components at the platform, one or more components at the first member, one or more components at the second members, one or more components at the base, or any combination of the foregoing.

Optionally, the base is configured to translate relative to a floor, a ceiling, or a wall, along a rectilinear path, a curvilinear path, or both.

Optionally, the base is moveably coupled to a floor.
Optionally, the base is moveably coupled to a ceiling.
Optionally, the base is moveably coupled to a wall.

A medical system includes the patient supporting device, and a treatment machine, wherein the patient supporting device is configured to place the patient at a treatment position with respect to the treatment machine.

Optionally, the patient supporting device is configured to place a first portion of the platform under an energy output of the treatment machine, and to move a second portion of the platform along a horizontal path while maintaining the first portion of the platform under the energy output.

Optionally, the patient supporting device is configured to move the second portion of the platform by moving the platform relative to the second member, moving the second member relative to the first member, moving the first member relative to the base, moving the base, or any combination of the foregoing.

Optionally, the patient supporting device is configured to place the platform at an orientation with respect to the treatment machine, and wherein when the platform is at the orientation, a longitudinal axis of the platform forms an acute angle with respect to a machine axis that extends from a front of the treatment machine to a back of the treatment machine.

Optionally, the treatment machine is configured to rotate an energy output while the platform is at the orientation.

Optionally, the medical system further includes an imaging machine, wherein the patient supporting device is configured to place the patient at an imaging position with respect to the imaging machine.

Optionally, the treatment machine and the imaging machine are in a side-by-side configuration.

Optionally, the treatment machine and the imaging machine are in a back-to-back configuration.

Optionally, the treatment machine and the imaging machine are in a front-to-front configuration.

Optionally, the imaging machine comprises a CT machine, a x-ray machine, a fluoroscope, a MRI machine, an ultrasound device, a PET machine, a SPECT machine, or a PET-CT machine.

Optionally, the patient supporting device is configured to move the platform in accordance with a first movement scheme when the platform is in a first coordinate system associated with the treatment machine, and to move the platform in accordance with a second movement scheme when the platform is in a second coordinate system associated with the imaging machine, the second movement scheme being different from the first movement scheme.

Optionally, the treatment machine comprises a radiation treatment machine.

Optionally, the radiation treatment machine comprises a ring gantry.

Optionally, the radiation treatment machine comprises an arm having an energy output and a collimator.

Optionally, the treatment machine comprises a proton treatment machine.

A medical method includes: providing a patient supporting device having a base, a first member rotatable relative the base about a first vertical axis, a second member rotatable relative to the first member about a second vertical axis, and a platform for supporting a patient, wherein the platform is rotatable relative to the second member about a third vertical axis; translating the base within a room; and operating the patient supporting device to place the patient at a treatment position with respect to a treatment machine.

Optionally, the act of operating the patient supporting device comprises rotating the platform relative to the second member about the third vertical axis.

Optionally, the act of operating the patient supporting device also comprises rotating the second member relative to the first member about the second vertical axis.

Optionally, the act of operating the patient supporting device also comprises rotating the first member relative to the base about the first vertical axis.

Optionally, the act of operating the patient supporting device also comprises moving the platform vertically.

Optionally, the act of translating the base comprises translating the base along a rectilinear path.

Optionally, the act of translating the base comprises translating the base along a curvilinear path.

Optionally, the patient supporting device is operated to place a first portion of the platform under an energy output of the treatment machine, and wherein the medical method further comprises moving a second portion of the platform along a horizontal path while maintaining the first portion of the platform under the energy output.

Optionally, the second portion of the platform is moved by moving the platform relative to the second member, moving the second member relative to the first member, moving the first member relative to the base, moving the base, or any combination of the foregoing.

Optionally, act of operating the patient supporting device is performed to place the platform at an orientation with respect to the treatment machine, and wherein when the platform is at the orientation, a longitudinal axis of the platform forms an acute angle with respect to a machine axis that extends from a front of the treatment machine to a back of the treatment machine.

Optionally, the medical method further includes rotating an energy output at the treatment machine while the platform is at the orientation.

Optionally, the act of rotating the energy output comprises rotating a ring gantry.

Optionally, the act of rotating the energy output comprises rotating an arm that comprises the energy output.

Optionally, the medical method further includes operating the patient supporting device to place the patient at an imaging position with respect to an imaging machine.

Optionally, the treatment machine and the imaging machine are in a side-by-side configuration.

Optionally, the treatment machine and the imaging machine are in a back-to-back configuration.

Optionally, the treatment machine and the imaging machine are in a front-to-front configuration.

Optionally, the imaging machine comprises a CT machine, a x-ray machine, a fluoroscope, a MRI machine, an ultrasound device, a PET machine, a SPECT machine, or a PET-CT machine.

Optionally, the medical method further includes delivering treatment radiation by the treatment machine.

Optionally, the medical method further includes delivering a proton beam by the treatment machine.

Optionally, the medical method further includes: operating the patient supporting device to move the platform in accordance with a first movement scheme when the platform is in a first coordinate system associated with the treatment machine; and operating the patient supporting device to move the platform in accordance with a second movement scheme when the platform is in a second coordinate system associated with the imaging machine, the second movement scheme being different from the first movement scheme.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

DESCRIPTION OF THE EMBODIMENTS

Figure 1:
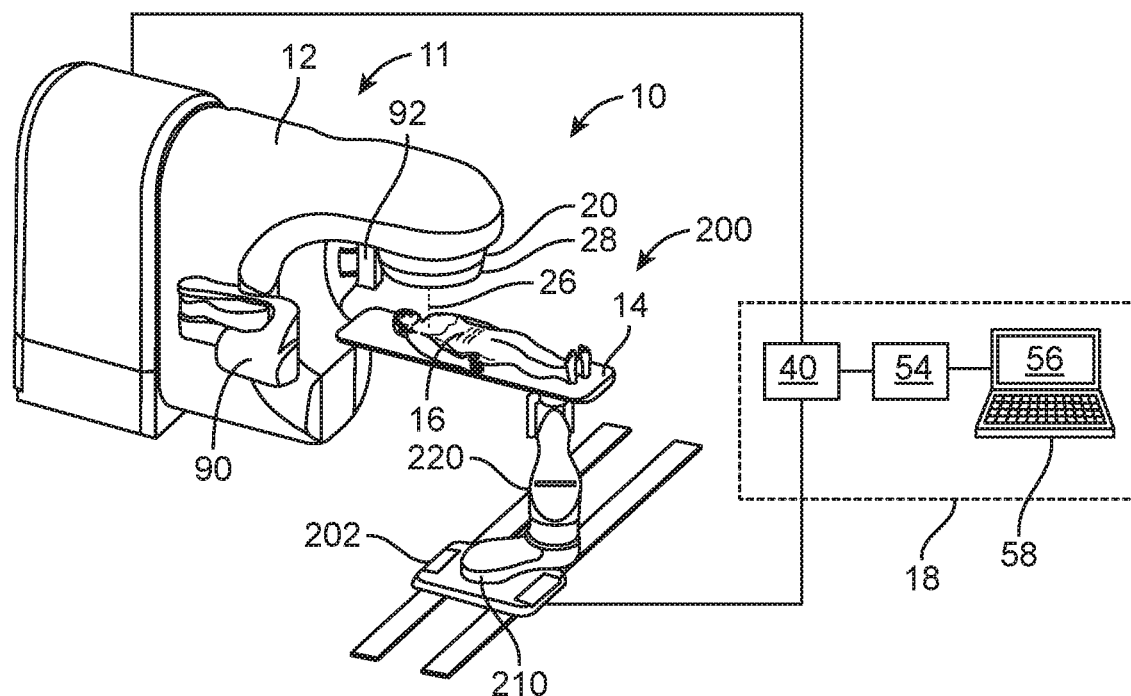
FIG. 1 illustrates a medical system for delivering treatment radiation with a patient supporting device in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1 illustrates a medical system 10 including a treatment machine 11 for delivering radiation. The treatment machine 11 includes a gantry 12 in a form of an arm. The treatment machine 11 also includes an energy output 20 that outputs a beam 26 of radiation towards a patient 16 while the patient 16 is supported on platform 14, and a collimator system 28 for controlling a delivery of the radiation beam 26. The energy output 20 can be configured to output a cone beam, a fan beam, or other types of radiation beams in different embodiments.

In the illustrated embodiments, the treatment machine 11 includes a treatment radiation source for providing treatment radiation energy. In other embodiments, in addition to being a treatment radiation source, the radiation source 20 can also be a diagnostic radiation source for providing diagnostic energy. In such cases, the treatment machine 11 will include an imager located at an operative position relative to the energy output 20 (e.g., under the platform 14). In some embodiments, the treatment energy is generally those energies of 160 kilo-electron-volts (keV) or greater, and more typically 1 mega-electron-volts (MeV) or greater, and diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source is able to generate X-ray radiation at a plurality of photon energy levels within a range anywhere between approximately 10 keV and approximately 20 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003. In further embodiments, the radiation source can be a diagnostic radiation source. In the illustrated embodiments, the energy output 20 is rotatably coupled to the gantry 12. In other embodiments, the energy output 20 may be located within a bore (instead of being located at an arm).

The medical system 10 also includes a control system 18 for controlling an operation of the treatment machine 11. In the illustrated embodiments, the control system 18 includes a processor 54, such as a computer processor, coupled to a control 40. The control system 18 may also include a monitor 56 for displaying data and an input device 58, such as a keyboard or a mouse, for inputting data. In the illustrated embodiments, the gantry 12 is rotatable about the patient 16, and during a treatment procedure, the gantry 12 rotates about the patient 16 (as in an arch-therapy). The operation of the radiation source, the collimator system 28, and the gantry 12 (if the gantry 12 is rotatable), are controlled by the control 40, which provides power and timing signals to the radiation source and the collimator system 28, and controls a rotational speed and position of the gantry 12, based on signals received from the processor 54. Although the control 40 is shown as a separate component from the gantry 12 and the processor 54, in alternative embodiments, the control 40 can be a part of the gantry 12 or the processor 54.

As shown in the figure, the platform 14 is a part of a patient supporting device 200. The patient supporting device includes a base 202, a first member 210, a second member 220, and the platform 14. The patient supporting device 200 will be described in further detail below.

In some embodiments, the treatment machine 11 may optionally include one or more imaging devices. For example, as shown in FIG. 1, the treatment machine 11 may further include a x-ray source 90 and an imager 92 located opposite from the x-ray source 90. The x-ray source 90 and the imager 92 may be configured to image the patient 16 before a delivery of treatment energy (e.g., for patient setup), and/or during a treatment energy delivery session (e.g., between deliveries of radiation beams). In other embodiments, the treatment machine 11 may not include the x-ray source 90 and the imager 92.

It should be noted that the treatment machine 11 is not limited to the configuration described above, and that the treatment machine 11 may have other configurations in other embodiments. For example, in other embodiments, the treatment machine 11 may have a different shape. In other embodiments, the energy output 20 of the treatment machine 11 may have different ranges of motions and/or degrees of freedom. For example, in other embodiments, the energy output 20 may be rotatable about the patient 16 completely through a 360° range, or partially through a range that is less than 360°. Also, in other embodiments, the energy output 20 is translatable relative to the patient 16. In further embodiments, the gantry 12 may be a ring gantry with a bore, and the energy output 20 may be located inside the bore of the gantry 12.

Figure 2:
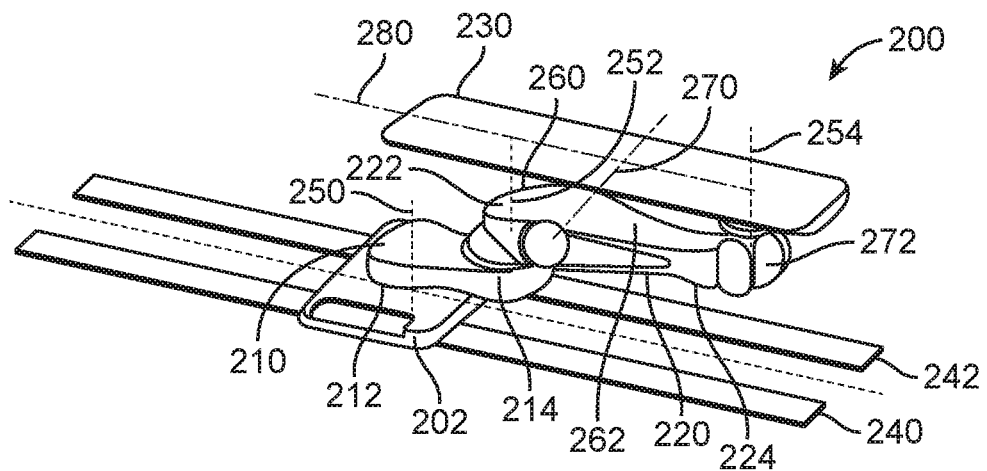
FIG. 2 illustrates the patient supporting device of FIG. 1.

FIG. 2 illustrates the patient supporting device 200 of FIG. 1. As shown in the figure, the patient supporting device 200 has a base 202, a first member 210 with a first end 212 and a second end 214, a second member 220 with a first end 222 and a second end 224, and a platform 230 (the platform 14 of FIG. 1). The base 202 is configured to move along a pre-determined path along a first rail 240 and a second rail 242. The first end 212 of the first member 210 is rotatably coupled to the base 202 so that the first member is rotatable relative to the base 202 about a first vertical axis 250. The first end 222 of the second member 220 is rotatably coupled to the second end 214 of the first member 210 so that the second member is rotatable relative to the first member 210 about a second vertical axis 252. The platform 230 is rotatably coupled to the second end 224 of the second member 220 so that the platform is rotatable relative to the second member 220 about a third axis 254.

In the illustrated embodiments, the second member 220 has a first member portion 260 and a second member portion 262. The first member portion 260 is rotatably coupled to the second member portion 262 so that the first member portion 260 can rotate relative to the second member portion 262 about a first horizontal axis 270. The platform 230 is rotatably coupled to the second member portion 262 so that the platform 230 can rotate relative to the second member portion 262 about a second horizontal axis 272. During use, the platform 230 can rotate relative to the second member portion 262 about the second horizontal axis 272, and the second member portion 262 can rotate relative to the first member portion 260 about the first horizontal axis 270, in synchronization, so that the platform 230 can move vertically (e.g., up and/or down).

Also, in the illustrated example, the platform 230 may be configured to rotate about its longitudinal axis 280.

In the example shown in the figure, the first member 210 is in a form of an arm, and the second member 220 is also in a form of an arm. Also, the first member portion 260 may be considered to be a part of an arm, and the second member portion 260 may be considered to be another part of the arm. In other embodiments, the first member 210 may have other form and/or shape, and may not necessarily be an arm. Similarly, in other embodiments, the second member 220 may have other form and/or shape, and may not necessarily be an arm.

In the illustrated embodiments, the base 202 is configured to move along a pre-determined path defined by the first rail 240 and/or the second rail 242. The first rail 240 and the second rail 242 have a rectilinear configuration, and therefore the base 202 is configured to move in a rectilinear path. In other embodiments, the rails 240, 242 may have a curvilinear configuration (e.g., an arc, a circular shape, etc.).

Figure 3:
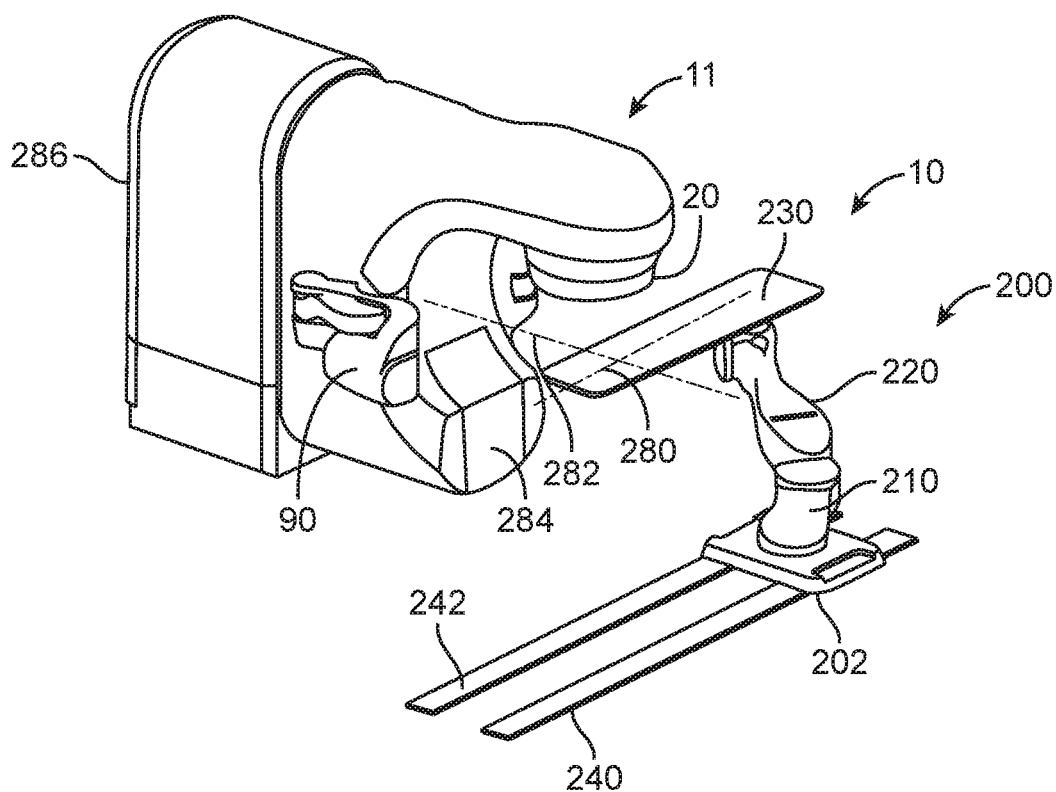
FIG. 3 illustrates the medical system of FIG. 1, particular showing the patient supporting device having a different configuration.

The configuration of the patient supporting device 200 is advantageous because it allows the platform 230 to be placed at different positions with respect to the treatment machine 11. For example, as shown in FIG. 3, the patient supporting device 200 may be operated to place the platform 230 at an orientation, where a longitudinal axis 280 of the platform 230 is perpendicular to a machine axis 282 extending from a front 284 of the treatment machine 11 to a back 286 of the treatment machine 11.

Figure 4:
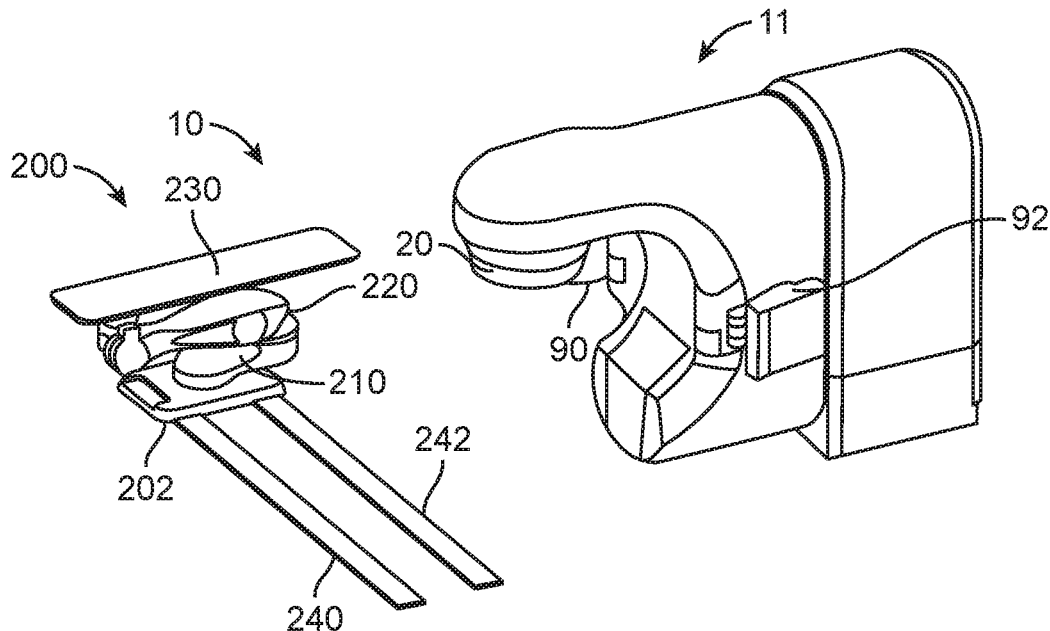
FIG. 4 illustrates the medical system of FIG. 1, particular showing the patient supporting device having a different configuration.

Also, before treatment is initiated, or after treatment is completed, the patient supporting device 200 may have the configuration shown in FIG. 4. In particular, the platform 230, the first member 210, the second member 220, and the base 202 collectively form a S-configuration that minimizes the extent of the space occupied by the patient supporting device 200. In such configuration, the patient supporting device 200 does not occupy significant space, and the patient supporting device 200 may allow the patient to conveniently get onto the platform 230 and/or to leave the platform 230.

Figure 5A:
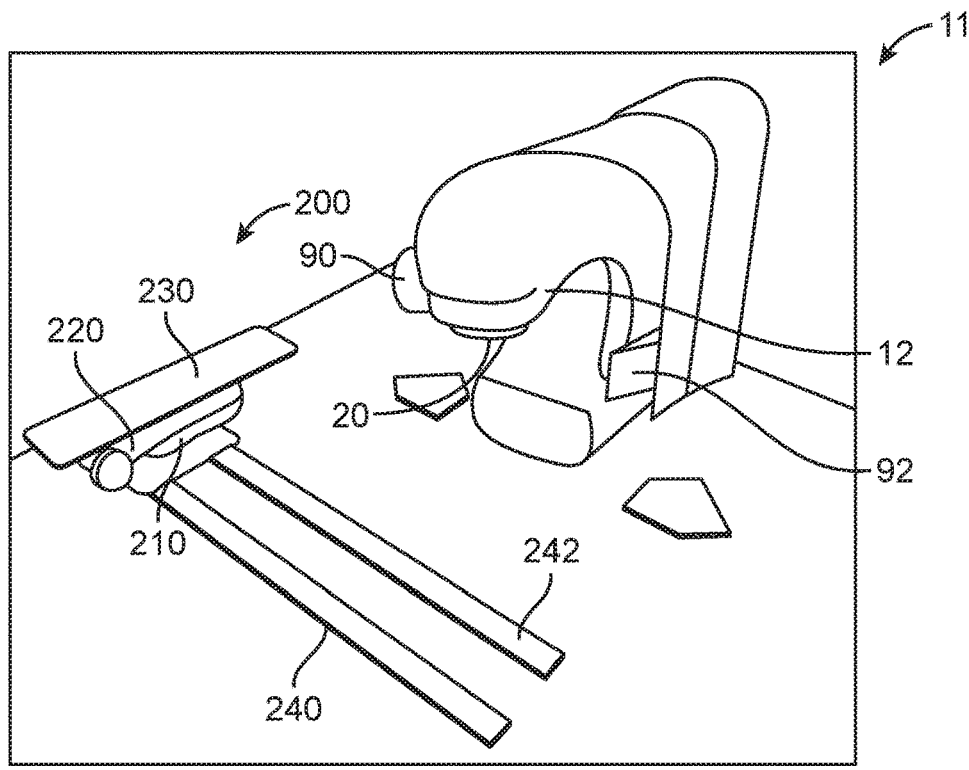
FIGS. 5A-5L illustrate the medical system of FIG. 1, particular showing different movement configurations for the treatment machine and the patient supporting device.

FIGS. 5A-5L illustrate examples of configurations that may be achieved by the patient supporting device 200 during a medical method. As shown in FIG. 5A, the patient supporting device 200 may be in a park position. While in the park position, the platform 230 is located above the second member 220, and the second member 220 is located above the first member 210. This configuration allows the patient supporting device 200 to be parked while minimizing the amount of space occupied by the patient supporting device 200. In some embodiments, the patient may be placed at the platform 230 while the patient supporting device 200 is in such park position. In other embodiments, the platform 230 may be moved to a patient-loading position for loading the patient onto the platform 230. For example, the base 202 of the patient supporting device 200 may be translated to move the platform 230 away from the park position to a patient-loading position. The patient may then be placed onto the platform 230.

Figure 5B:
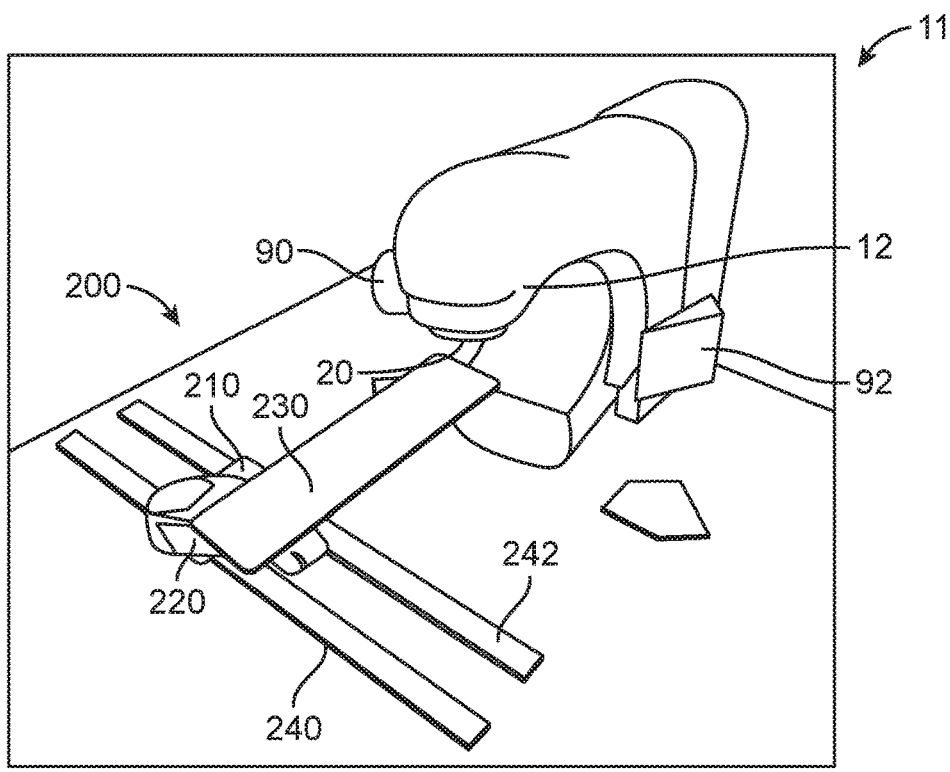

Next, the patient supporting device 200 may be operated to move the platform 230 so that the longitudinal axis 280 of the platform 280 corresponds with the machine axis 282 (FIG. 5B). For example, the base 202 may be translated along the rails, the first member 210 may be rotated relative to the base 202, the second member 220 may be rotated relative to the first member 210, the platform 230 may be rotated relative to the second member 220, or any combination of the foregoing may be performed, in order to desirably position the platform 230. While in the configuration shown, a patient setup procedure may be performed to align the patient with respect to the treatment machine 11. For example, certain region of the patient may be placed at the treatment position (e.g., isocenter position) with respect to the treatment machine 11.

After the patient setup procedure, the treatment machine 11 may then be operated to treat the patient. For example, as shown in FIG. 5C, the arm of the treatment machine 11 may be rotated to thereby place the energy output 20 at different gantry angles to deliver energies towards the patient from different angles.

Figure 5C:
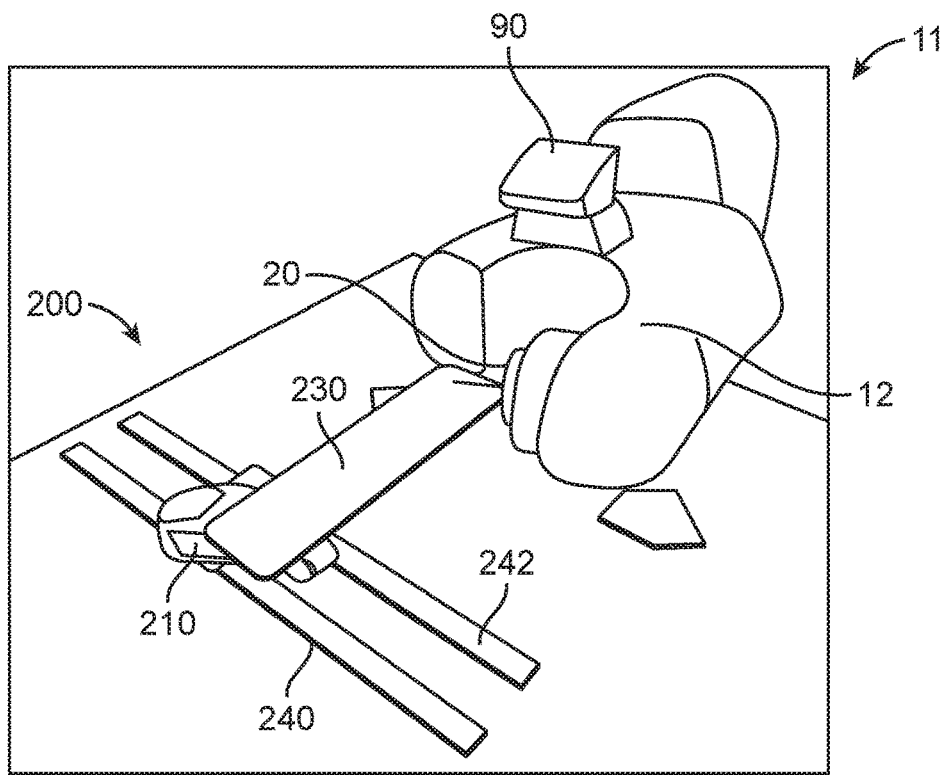

In the example shown in FIG. 5C, the energy output 20 rotates around the treatment position while the platform 230 is at an orientation where the longitudinal axis 280 of the platform 230 corresponds with the machine axis 282 of the treatment machine 11. In other embodiments, the platform 230 may be positioned such that the longitudinal axis 280 of the platform 230 is at an acute angle, at a 90° angle, or at an angle that is larger than 90° but less than 180°, with respect to the machine axis 282. While the platform 230 is at such position, the energy output 20 of the treatment machine 11 may be rotated around the treatment position to deliver energies towards the patient from different gantry angles.

Figure 5D:
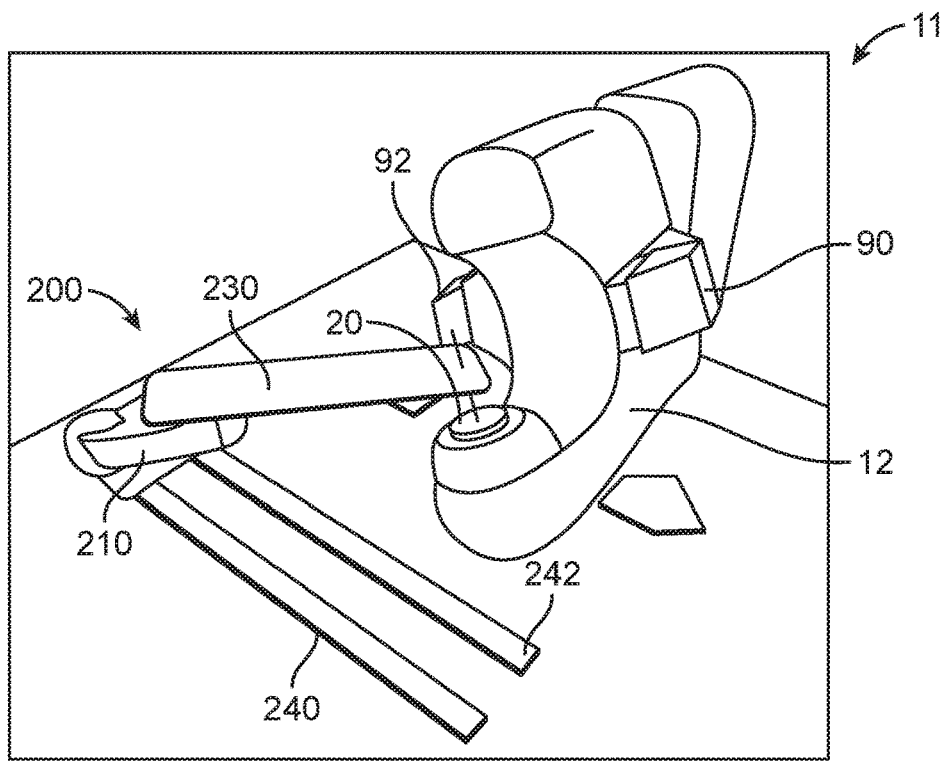
Figure 5E:
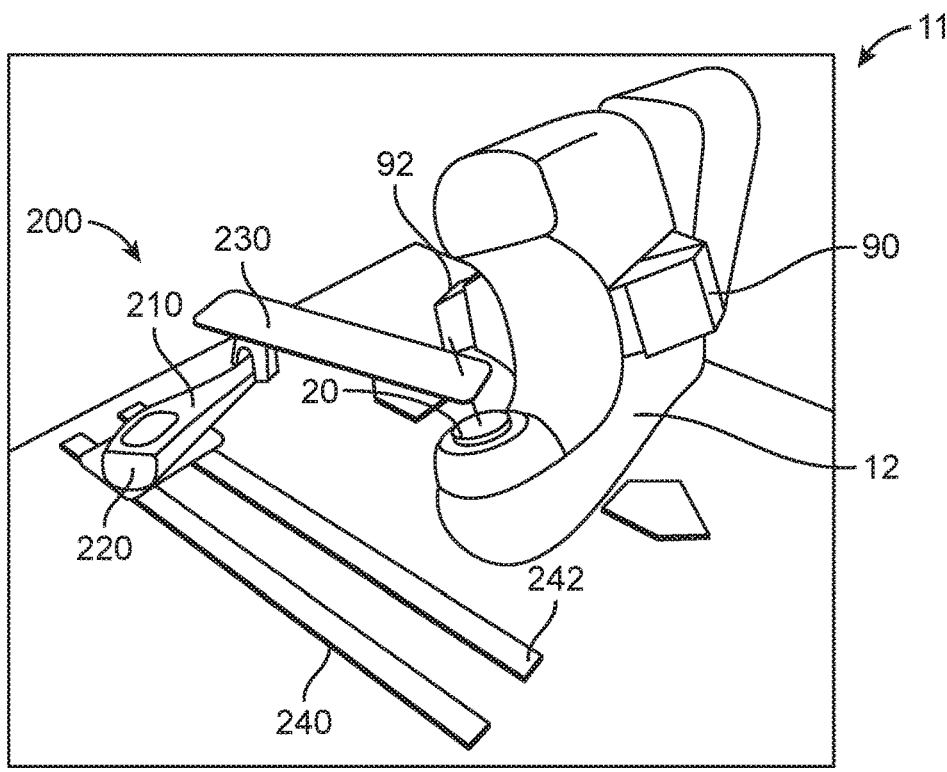
Figure 5F:
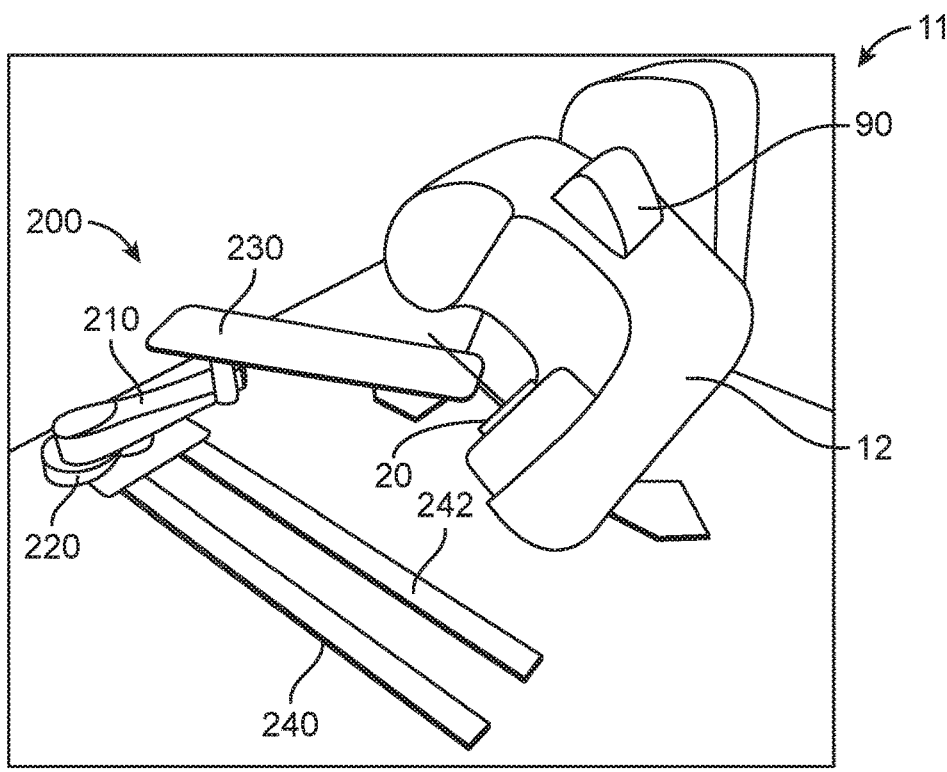
Figure 5G:
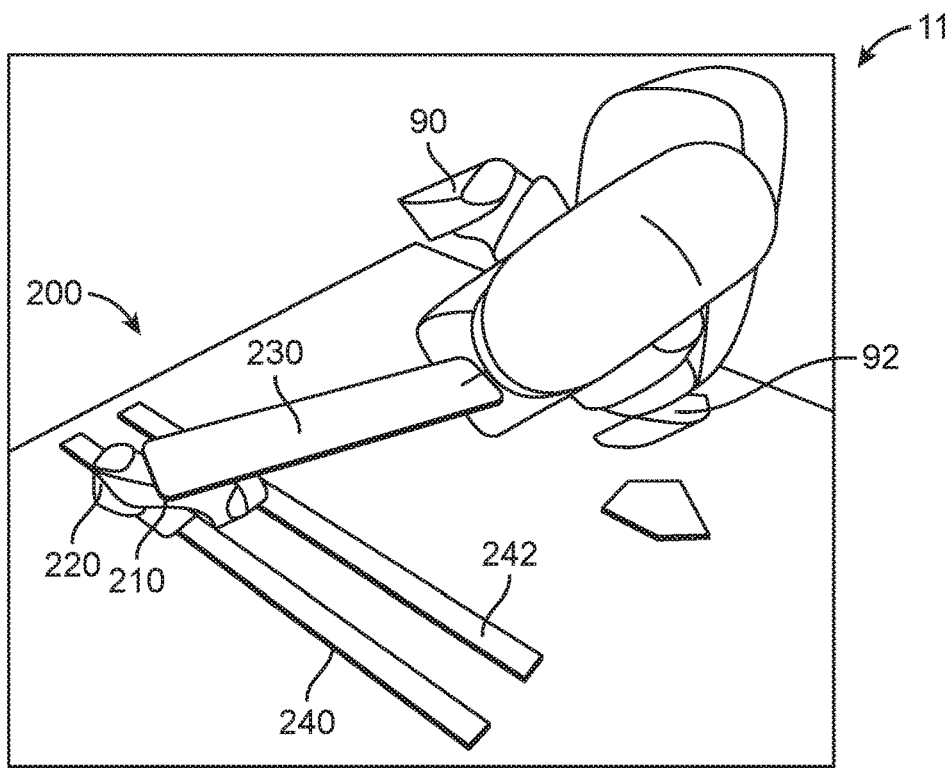
Figure 5H:
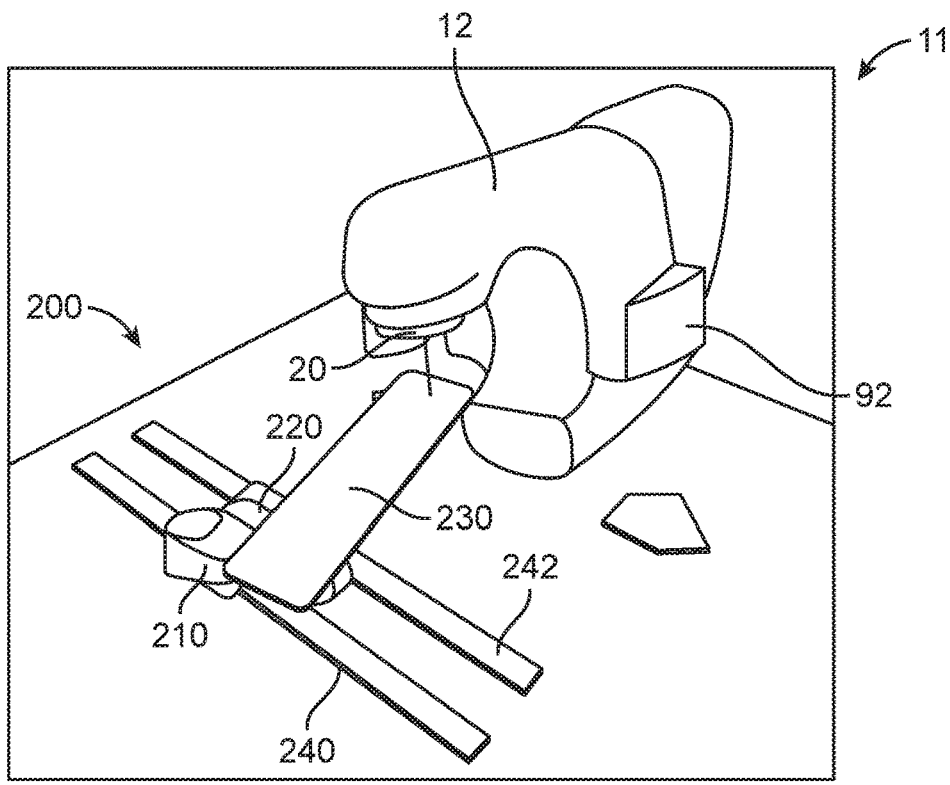
Figure 5I:
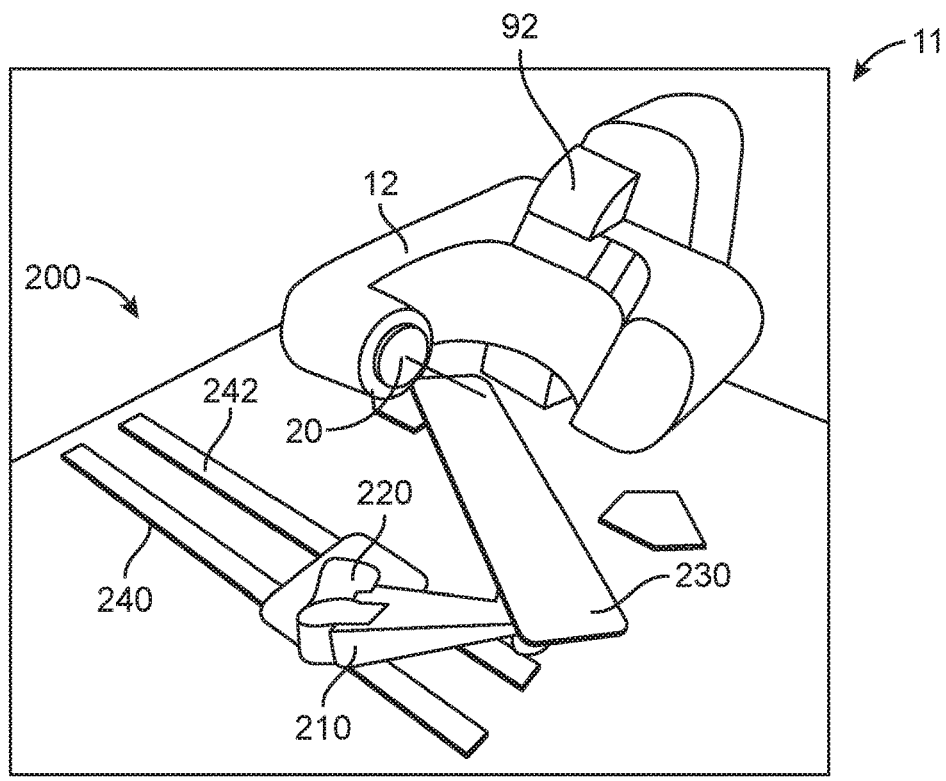
Figure 5J:
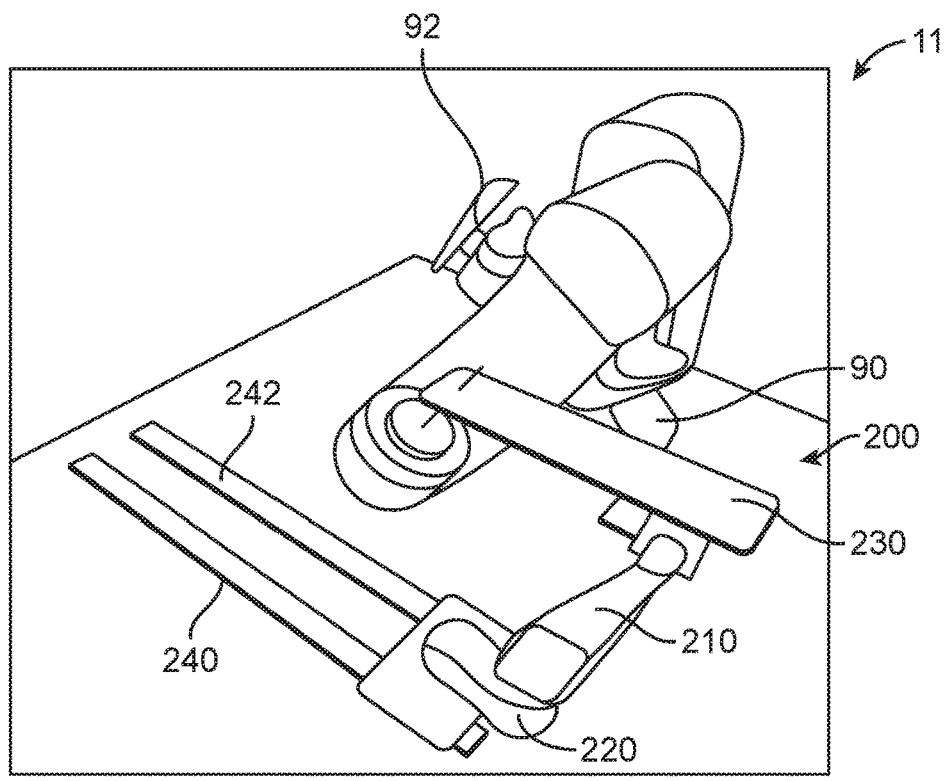
Figure 5K:
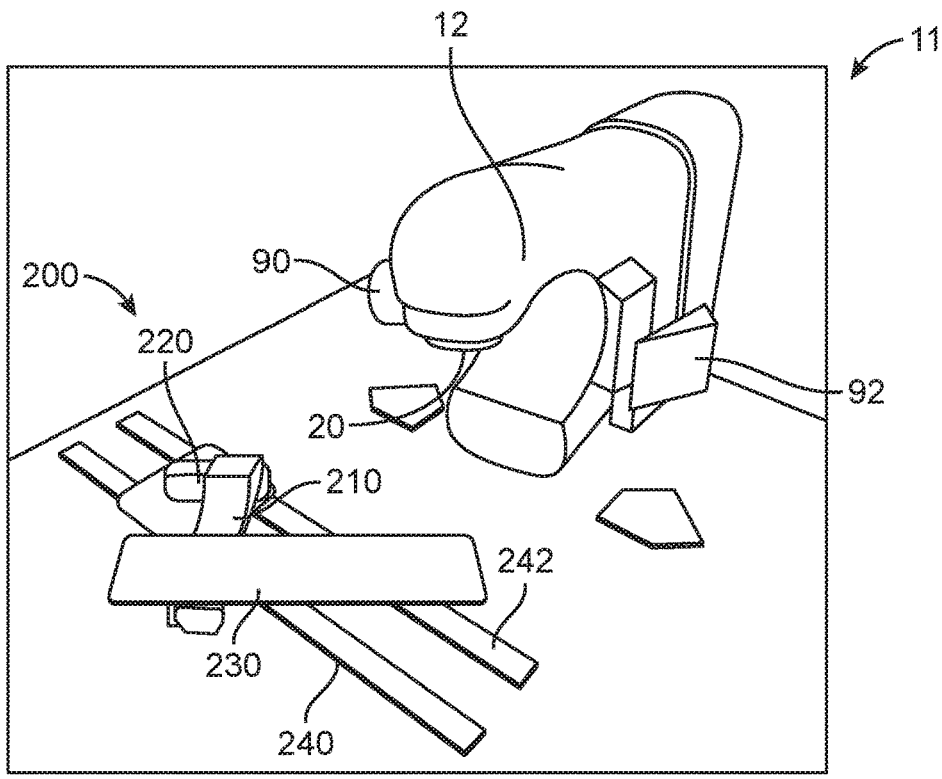
Figure 5L:
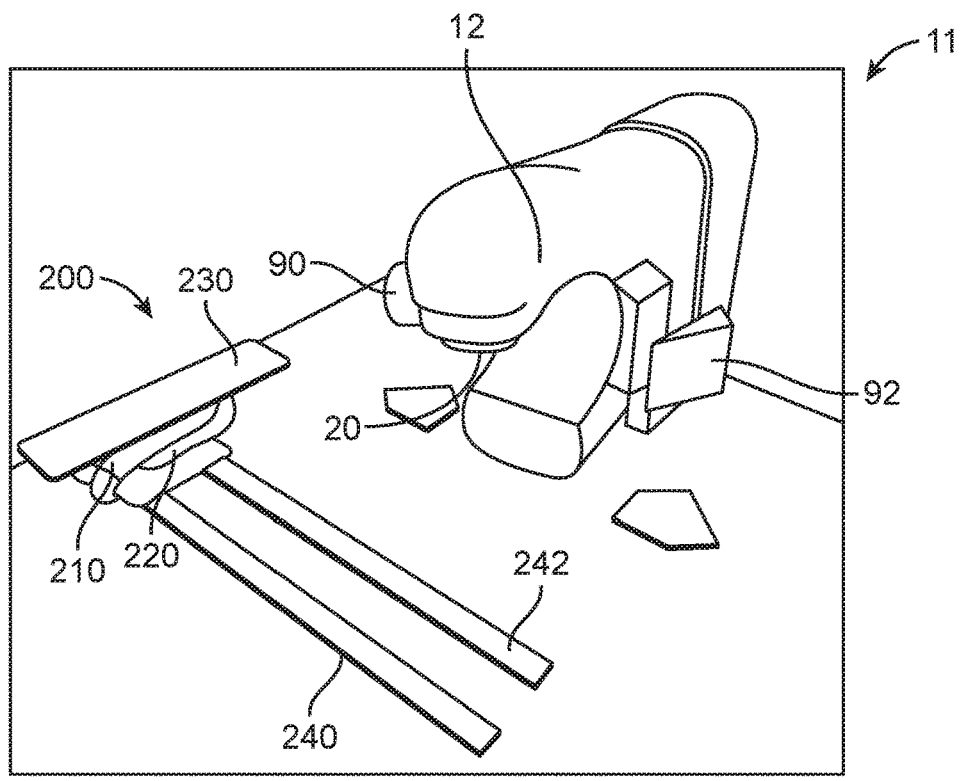

In some cases, instead of rotating the energy output 20 around the treatment position while the platform 230 is stationary, the platform 230 may be positioned while the energy output 20 is stationary. For example, as shown in FIGS. 5D-5E, while the arm with the energy output 20 is stationary at the position shown, the patient supporting device 200 may be operated to rotate the platform 230 from the position shown in FIG. 5C to the position shown in FIG. 5D, and also from the position shown in FIG. 5D to the position shown in FIG. 5E. Such movement results in a portion of the platform 230 remaining in a field-of-view of the energy output 20 while the platform 230 is rotated within a horizontal plane. In some cases, a surface point of the platform 230 may remain stationary while the platform 230 is rotated about a vertical axis extending through the surface point.

In one implementation, the above movement of the platform 230 (from the position of FIG. 5C to the position of FIG. 5D, and then to the position of FIG. 5E) may be achieved by moving the platform 230 relative to the second member 220, moving the second member 220 relative to the first member 210, moving the first member 210 relative to the base 202, moving the base 202, or any combination of the foregoing. In some cases, if multiple components of the patient supporting device 200 are moved, the multiple components may be moved simultaneously. Alternatively, the multiple components may be moved in sequence such that one component is moved first, and then another component is moved afterwards. In either case, the energy output 20 may deliver treatment energy towards the patient while one or more of the components (e.g., the base 202, the first member 210, the second member, 220, the platform 230, etc.) of the patient supporting device 200 are moving, or when the components of the patient supporting device 200 have stopped moving. For example, when the platform 230 is moved along a path, the components of the patient supporting device 200 may stop moving at certain points along the path to allow the energy output 20 of the treatment machine 11 to deliver energies towards the patient.

In the above example, the energy output 20 is located below the elevation of the platform 230 while the platform 230 is rotated about a vertical axis extending through a field-of-view of the energy output 20. In other embodiments, the energy output 20 may be at other positions while the platform 230 is rotated about the vertical axis. For example, the energy output 20 of the treatment machine 11 may be directly above the platform 230, at the same elevation as that of the platform 230, or may be at other positions that are above or below the elevation of the platform 230.

In some cases, instead of moving (e.g., rotating) the platform 230 while the energy output 20 of the treatment machine 11 is stationary, both the platform 230 and the energy output 20 of the treatment machine 11 may be positioned. For example, as shown in FIGS. 5E-5J, the platform 230 and the energy output 20 of the treatment machine 11 may be moved simultaneously so that the platform 230 and the energy output 20 are moved from the respective positions shown in FIG. 5E to the respective positions in FIG. 5F, and then to the respective positions in FIG. 5G, and then to the respective positions in FIG. 5H, and then to the respective positions in FIG. 5I, and then to the respective positions in FIG. 5J.

In one implementation, the above movement of the platform 230 (from the position of FIG. 5E to the position of FIG. 5F, to the position of FIG. 5G, to the position of FIG. 5H, to the position of FIG. 5I, and to the position of FIG. 5J) may be achieved by moving the platform 230 relative to the second member 220, moving the second member 220 relative to the first member 210, moving the first member 210 relative to the base 202, moving the base 202, or any combination of the foregoing. In some cases, if multiple components of the patient supporting device 200 are moved, the multiple components may be moved simultaneously. Alternatively, the multiple components may be moved in sequence such that one component is moved first, and then another component is moved afterwards. In either case, the energy output 20 may deliver treatment energy towards the patient while one or more of the components (e.g., the base 202, the first member 210, the second member, 220, the platform 230, etc.) of the patient supporting device 200 are moving, and/or while the energy output 20 is moving. Alternatively, the energy output 20 may deliver treatment energy towards the patient when the components of the patient supporting device 200 have stopped moving, and when the energy output 20 has stopped moving. For example, when the platform 230 is moved along a path, the components of the patient supporting device 200 may stop moving at certain points along the path to allow the energy output 20 of the treatment machine 11 to deliver energies towards the patient. Similarly, when the energy output 20 of the treatment machine 11 is moved along a path, the energy output 20 may stop moving at certain points along the path to allow the energy output 20 to deliver energies towards the patient. Alternatively, the delivery of energies may occur simultaneously while the components of the patient supporting device 200 are moving, and/or while the energy output 20 of the treatment machine 11 is moving.

After the patient has been treated, the platform 230 may then be moved to a patient-unloading position to unload the patient. For example, the patient supporting device 200 may be operated to move the platform 230 to the position shown in FIG. 5K. Alternatively, the patient supporting device 200 may be operated to move the platform 230 to the position shown in FIG. 5L.

As illustrated in the above embodiments, the patient supporting device 200 is advantageous because the patient supporting platform 230 (and therefore the patient) to be placed at a variety of positions and orientations with respect to the treatment machine 11. In combination with the movement of the energy output 20 of the treatment machine 11, the various degrees of movement of the patient supporting device 200 allow treatment energies to be delivered to the patient from many different angles that were not possible in existing solutions. Also, the configuration of the patient supporting device 200 allows larger reach to other machines next to the treatment machine, and increases positional flexibility. Furthermore, because the patient supporting device 200 can be folded to assume a narrow profile, the patient supporting device 200 can be parked close to a wall. In addition, the length of the rail system (including the rails 240, 242) can be easily adapted according to treatment room size or usage of the system. This flexibility allows installations of the rail system and the patient supporting device 200 for various different room layouts.

Also, the movement of the base 202 along a path (e.g., along one or more rails) is advantageous because it may allow the platform 230 to be moved to a certain position faster and more effectively. If the base 202 is not moveable along a path, it may take longer for the platform 230 to reach certain positions because of the articulation of the arm relative to the room and the treatment machine.

It should be noted that the movements and positioning of the various components of the patient supporting device 200 should not be limited to the examples described, and that the patient supporting device 200 may achieve other types of movements and positioning. For example, in other embodiments, the platform 230 may be translated vertically (e.g., up and/or down) while the orientation of the platform 230 is maintained. Such may be accomplished by synchronously rotating the second member 220 relative to the first member 210 about the first horizontal axis in a first direction, and simultaneously rotating the platform 230 relative to the second member 220 about the second horizontal axis in a second direction that is opposite the first direction. In other embodiments, the platform 230 may be translated horizontally along a path that corresponds with (e.g., parallel to) the machine axis 282 of the treatment machine 11. Such may be accomplished by synchronously rotating the first member 210 relative to the base 202 about the first axis 250 in a first direction, rotating the second member 220 relative to the first member 210 about the second axis 252 in a second direction opposite the first direction, and rotating the platform 230 relative to the second member 220 about the third axis 254 in the first direction. In still further embodiments, the platform 230 may be translated horizontally along a path that is parallel to the floor. Such may be accomplished by translating the base 202.

Also, in any of the embodiments described herein, the patient supporting device 200 may be configured to move at a speed that is sufficient for dynamic treatment. For example, the patient supporting device 200 may be configured to move in a path with a speed that corresponds (e.g., complements) with a motion speed of the treatment machine 11 (e.g., the speed of the rotating energy output 20) and/or the rate at which treatment energies are being delivered. Also, in some cases, the patient supporting device 200 may be configured to move with a sufficiently fast speed to allow the patient supporting device 200 to compensate for a breathing motion of the patient. For example, the patient supporting device 200 may be configured to move the patient in order to at least partially compensate for a breathing motion of the patient, thereby allowing breathing gating to be used to deliver treatment energies.

In addition, in any of the embodiments described herein, the patient supporting device 200 may be configured to move the platform 230 in synchronization or in correspondence with a movement or position of the energy output 20. For example, the platform 230 may be moved so that a point at the patient (e.g., an isocenter) is maintained at a certain prescribed distance or a certain prescribed range of distances from the energy output 20. Accordingly, regardless of the position of the energy output 20, the isocenter is maintained at a fixed distance or within a fixed distance range from the energy output 20. The movement of the platform 230 may be dynamically performed simultaneously with a movement of the energy output 20. Alternatively, the movement of the platform 230 may be performed after the energy output 20 has moved, so that the movements of the platform 230 and the energy output 20 are staggered. Furthermore, in some cases, the soured-axis-distance (SAD) may be extended compared to the scenario in which the platform 230 is stationary and the energy output 20 is rotated around the platform 230. Such can be accomplished by moving the platform 230 in a direction that is away from the energy output 20, thereby increasing the SAD. During treatment, as the energy output 20 rotates around a space, the patient supporting device 200 also rotates the platform 230 around the same space in synchronization or in correspondence with the energy output 20. This allows the energy output 20 to always be aimed at a treatment target in the patient supported on the platform 230, which both the energy output 20 and the platform 230 on opposite sides of the space are rotated in correspondence with each other.

In the above embodiments, the treatment machine 11 has been described as having a rotatable arm that includes an energy output 20 and a collimator. In other embodiments, instead of the rotatable arm, the treatment machine 11 may have a ring gantry that carries the energy output 20. In such cases, during treatment, the patient supporting device 200 may be operated to place a part of the patient into a bore, and the ring gantry may be rotated around the patient to allow the energy output 20 to deliver treatment energies from different angles.

In addition, in any of the embodiments described herein, the platform 230 may be a removeable couch top. For example, the platform 230 may be detachably coupled to a connector that is at the second end of the second member 220. In some cases, the platform 230 may be removed from the rest of the patient supporting device 200, and the patient may be placed on top of the platform 230 for patient setup. The placement of the patient on the platform 230 may be performed in the treatment room where the patient supporting device 200 is located, or may be performed in another room. In one implementation, the patient may be positioned such that a reference location at the patient relative to the platform 230 is achieved. After that is set up, the platform 230 with the patient may then be attached to the connector at the patient supporting device 200. Furthermore, in some embodiments, the movement of the platform 230 with the patient to attach the platform 230 with the rest of the patient supporting device 200 may be performed automatically using a robotic device (e.g., a tool-changer).

In further embodiments, the patient supporting device 200 may also include one or more positional indicators for allowing a position of the patient supporting device 200 to be determined. For example, the patient supporting device 200 may include a positioning system that allows its position relative to some global coordinate system be determined. The positioning system may include one or more components at the platform 230, one or more components at the first member 210, one or more components at the second member 202, one or more components at the base 202, or any combination of the foregoing. The component may be a signal emitter, a signal receiver, a fiducial, a marker, etc. In other embodiments, a component may be a sensor for sensing a signal, or may be a fiducial that is configured for sensing, that can be used to derive a position.

In another example, the patient supporting device 200 may include multiple positional indicators at the respective moving parts (e.g., the base 202, the first member 210, the first member portion 260 of the second member 220, the second member portion 262 of the second member 220, and the platform 230). The positional indicators may have respective energy sources for emitting positional energies (beacons), and there may be one or more detectors in the treatment room for detecting such positional energies. Based on the detected positional energies, the processing unit may then determine the positions and orientations of the various components of the patient supporting device 200. In other embodiments, the beacons may be passive devices.

In another example, the positional indicators may include one or more markers at the platform 230, one or more markers at the first member 210, one or more markers at the second member 220, and one or more markers at the base 202. The markers may be configured to be detected using one or more cameras, or other types of sensing device(s).

In further embodiments, the patient supporting device 200 may include an imaging system for imaging the patient. For example, the patient supporting device 200 may include an energy source for providing imaging energy, and an imager for generating an image of a patient (e.g., an internal part of the patient) based on the imaging energy after it has penetrated through the patient. By means of non-limiting examples, the imaging system at the patient supporting device 200 may be a radiation imaging system, an ultrasound imaging system, a MRI system, a fluoroscope, a CT system, a PET system, a SPECT system, a CT-PET system, etc. During use, the imaging system at the patient supporting device 200 may be used to image the patient to determine a position and/or a shape of target and/or critical organ. Such may be performed during a patient setup procedure, and/or during treatment (e.g., between deliveries of treatment energies).

Also, in any of the embodiments described herein, instead of having the platform 230 that is completely horizontal to support the entire patient horizontally, the platform 230 may have other configurations in other embodiments. For example, in other embodiments, the platform 230 may have a form of a chair to support the patient in an upright position. In one implementation, the platform 230 may have a first platform portion and a second platform portion that is rotatably coupled to the first platform portion. The platform portions may be operated so that both platform portions are oriented horizontally, thereby providing a completely horizontal supporting surface for supporting the patient horizontally. In another method of use, one of the platform portions may be rotated to be in an upright position, thereby creating a chair-like supporting structure for supporting the patient in an upright position.

Furthermore, in any of the embodiments described herein, the patient supporting device 200 may include one or more force and/or torque sensor for load measurement. In one implementation, the platform 230 may have a force sensor for measuring an amount of load being supported by the platform 230. The measurement may be transmitted to a processing unit, which calculates an amount of deflection resulted from such load. The processing unit may then operate the patient supporting device 200 (e.g., rotate the platform 230 about a horizontal axis that is perpendicular to the longitudinal axis of the platform 230) to compensate for such deflection. Because the patient supporting device 200 is configured to support load using cantilever-action, the amount of deflection due to heavy load supported by the platform 230 may be significant. The above feature may allow the deflection to be compensated. In other embodiments, the patient supporting device 200 may not support load using cantilever-action, and the deflection due to patient load on the platform 230 may not be significant.

In addition, in any of the embodiments described herein, the patient supporting device 200 and/or the treatment machine 11 may include one or more cameras for monitoring the patient. The one or more cameras may be used to sense one or more markers (e.g., one or more light emitting or light reflecting markers, one or more reference locations at the patient that function as marker(s), etc.). In some embodiments, the sensed markers may be used to determine a position of a patient part. For example, the sensed markers may be positionally related to a breathing movement of the patient. In such cases, the sensed markers may be processed by a processing unit, which determines one or more breathing phases of the patient. Also, in some embodiments, the one or more cameras may generate images for monitoring a position of the patient. The processing unit may process such images to ensure that the patient is at an intended position, and/or to provide collision detection and avoidance. It should be noted that one or more of the camera(s) may be a depth sensing camera. In one implementation, the patient supporting device 200 may include a depth sensing camera attached thereto. During use, the depth sensing camera detects a surface of the patient, and the processing unit generates a surface model representing the surface of the patient. While treatment is being performed, the patient supporting device 200 and the treatment machine 11 may move. The processing unit monitors objects next to the patient. If the processing unit determines that an object (e.g., the arm 12 of the treatment machine 11) is getting too close to the patient (e.g., within a threshold distance from the surface model), the processing unit may then generates a warning signal and/or a control signal to stop or pause the treatment. For example, the processing unit may generate a control signal to stop a movement of the treatment machine 11 and/or a movement of the patient supporting device 200. The processing unit may also generate a control signal to stop a delivery of treatment energies by the treatment machine 11. In some cases, one or more proximity sensors may be employed to determine whether the patient is too close to component(s) of the treatment machine 11.

Also, in the above embodiments, the treatment machine 11 has been described with reference to providing treatment radiation. In other embodiments, the treatment machine 11 may be configured to provide other types of treatment energy. For examples, in other embodiments, the treatment machine 11 may be configured to provide proton beam for proton therapy, treatment ultrasound energy, radiofrequency energy, etc. In addition, in other embodiments, the radiation source may be a proton source for delivering protons to treat a patient, an electron source for delivering electrons, or other types of particle source for delivering other types of particles for treating patient.

Figure 6A:
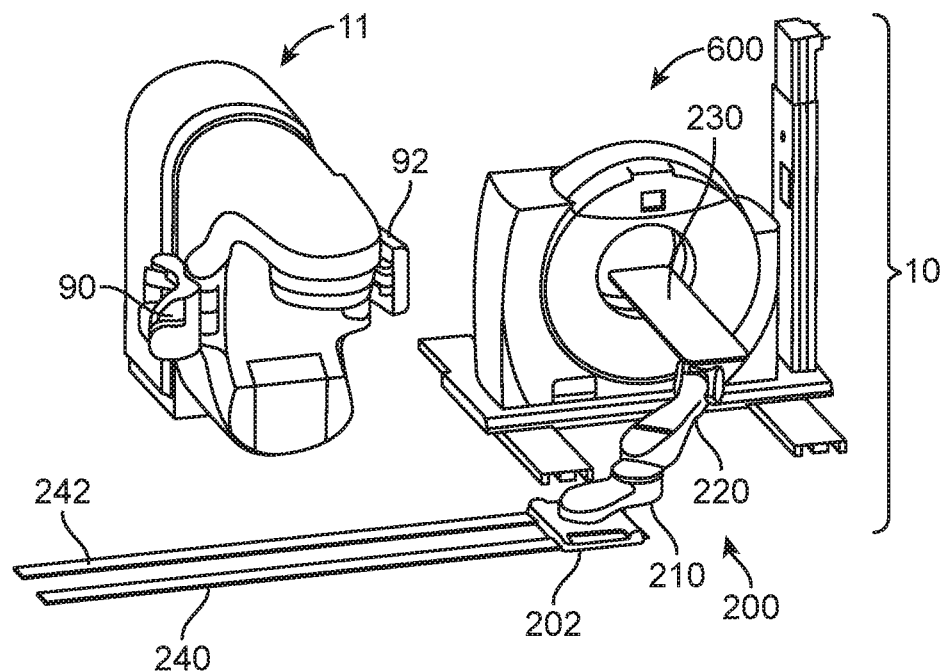
FIG. 6A illustrates a medical system having a treatment machine, an imaging machine, and a patient supporting device.

In any of the embodiments described herein, the treatment system may optionally further include an imaging machine located next to the treatment machine 11. FIG. 6A illustrates an example in which the treatment system includes an imaging machine 600 placed next to the treatment machine 11 in a side-by-side configuration. By means of non-limiting examples, the imaging machine 600 may be a CT machine, a x-ray machine, a fluoroscope, a MRI machine, an ultrasound device, a PET machine, a SPECT machine, or a PET-CT machine. In the side-by-side configuration, both a front of the treatment machine 11 and a front of the imaging machine 600 are facing the same direction. During use, the patient supporting device 200 may be configured to place the patient at a treatment position with respect to the treatment machine 11, and also at an imaging position with respect to the imaging machine 600. For example, before a treatment session begins, the patient supporting device 200 may place the patient at the imaging position to allow the imaging machine 600 to image the patient. The image(s) from the imaging machine 600 may be used to confirm the position and shape of target (e.g., tumorous tissue), and/or be used to perform patient setup. After the image(s) is obtained, the patient supporting device 200 may then move the patient from the imaging position to the treatment position, to thereby allow the treatment machine 11 to deliver treatment energies towards the patient. During treatment, if desired, the patient supporting device 200 may move the patient from the treatment position to the image position to allow the imaging machine 600 to obtain additional image(s) of the patient. The additional image(s) may be used to determine position and/or shape of target, which in turn, may be used to update or modify a treatment plan.

In some embodiments, the patient supporting device 200 may be configured to make motions in multiple different coordinate systems corresponding with respective different machines. For example, the control of the patient supporting device 200 may be configured to operate the patient supporting device 200 to move in a first path within a first coordinate system (e.g., one for the treatment machine 11), and to operate the patient supporting device 200 to move in a second path different from the first path within a second coordinate system (e.g., one for the imaging machine 600).

Figure 6B:
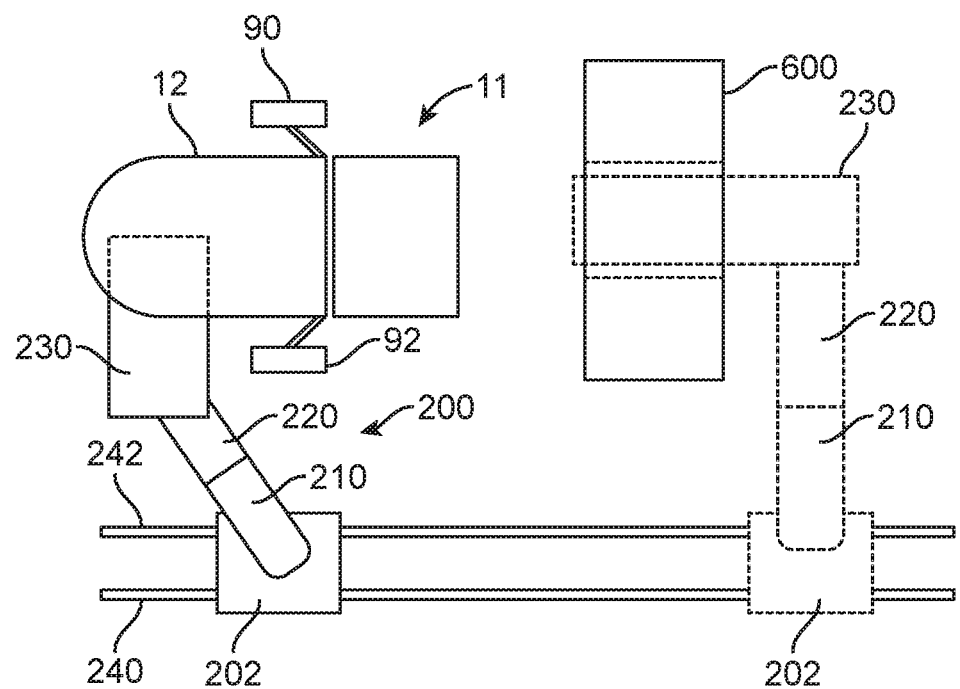
FIG. 6B illustrates another medical system having a treatment machine, an imaging machine, and a patient supporting device.
Figure 6C:
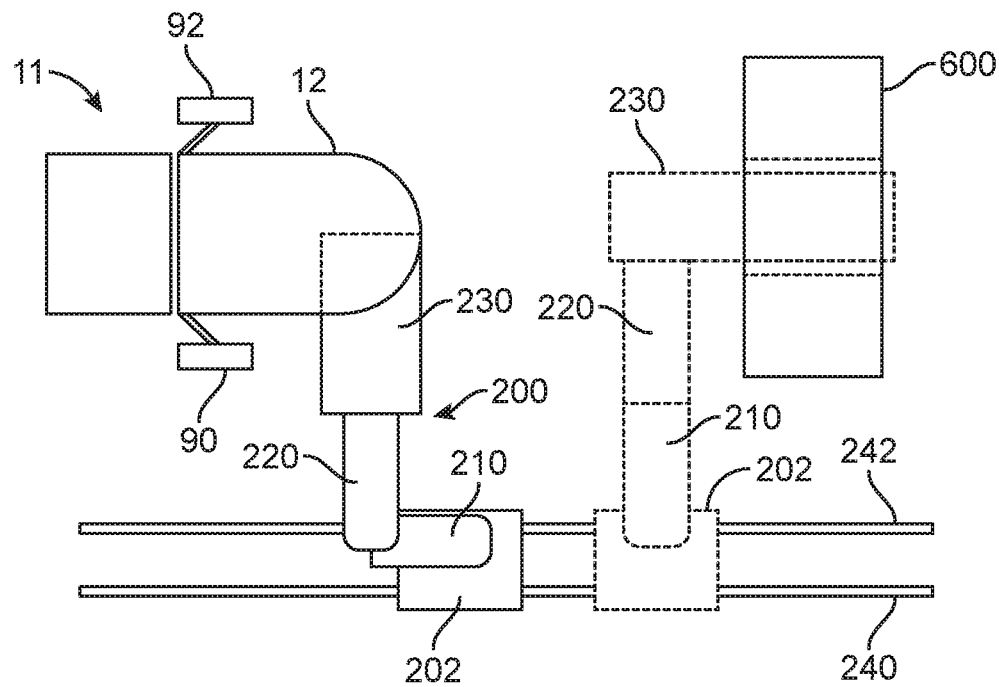
FIG. 6C illustrates another medical system having a treatment machine, an imaging machine, and a patient supporting device.
Figure 6D:
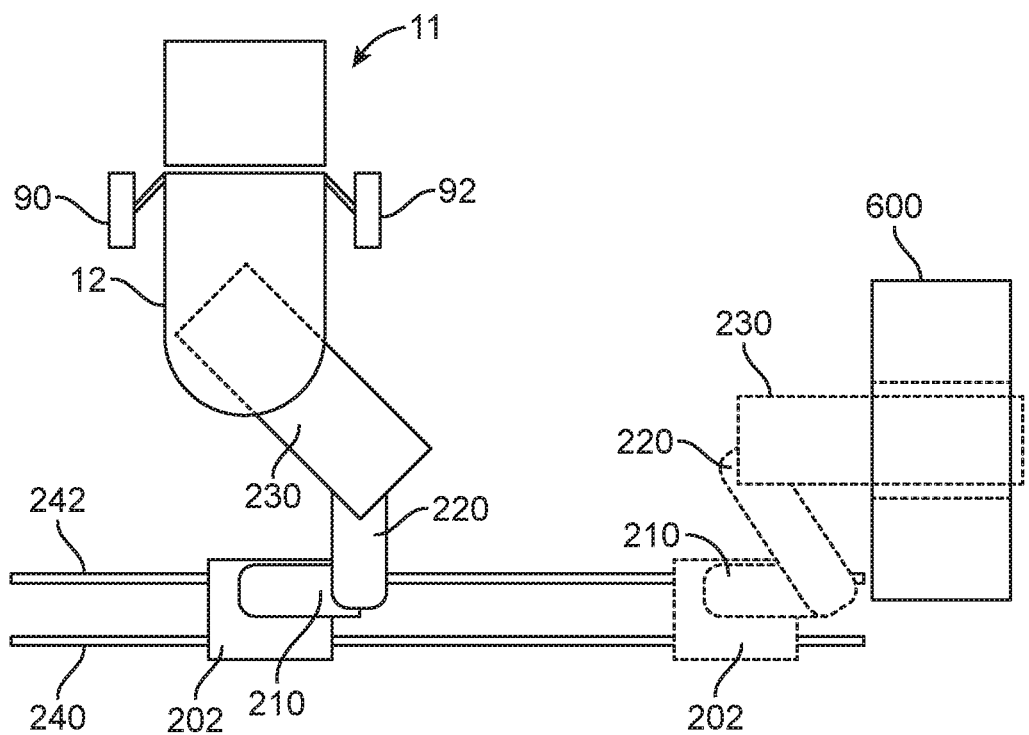
FIG. 6D illustrates another medical system having a treatment machine, an imaging machine, and a patient supporting device.

In other embodiments, instead of the side-by-side configuration, the treatment machine 11 and the imaging machine 600 may be placed next to each other in a back-to-back configuration (in which the back of the treatment machine 11 faces towards the back of the imaging machine 600) (FIG. 6B), or in a front-to-front configuration (in which the front of the treatment machine 11 faces towards the front of the imaging machine 600) (FIG. 6C). In further embodiments, the treatment machine 11 and the imaging machine 600 may be placed next to each other at 90° (or other angles) with respect to each other (FIG. 6D).

In any of the embodiments described herein, the operation of the patient supporting device 200 may be achieved using a control that generates control signals for causing one or more of the components (e.g., base 202, first member 210, second member 220, platform 230) of the patient supporting device 200 to move. The control may include circuitry and/or algorithm for generating the control signals. In some cases, the control may include a processing unit configured to receive and process a treatment plan, which prescribes the condition and/or the manner for moving the platform 230. The processing unit may generate the control signals based on parameters provided from the treatment plan. For example, the treatment plan may include parameters for indicating that the platform 230 be moved from position X to position Y when certain criteria are met. The criteria may be a position of the energy output of the treatment machine 11, a total accumulated dose delivered to the patient, an amount of dose delivered to target, an amount of dose delivered to critical organ, etc. In some embodiments, the control for the patient supporting device 200 may include a member control module for controlling movement of the first member 210 and/or the second member, a base control module for controlling a movement of the base 202, and a platform control module for controlling a movement of the platform 230 relative to the second member 220. Also, in some embodiments, the treatment plan may prescribe the positions and orientations of the platform 230 to be accomplished at certain time points or certain conditions, and the control of the patient supporting device 200 may include an analysis module configured to determine which component(s) (e.g., the base 202, the first member 210, the second member 220, the platform 230) to move and amount(s) of movement to accomplish the prescribed positions and orientations of the platform 230.

Also, in the above embodiments, the rails 240, 242 are described as being at the floor (e.g., they can be mounted on or in the floor). In other embodiments, the rails 240, 242 may be mounted at the ceiling of the operating room. In further embodiments, the rails 240, 242 may be mounted to a wall of the operating room. Regardless of where the rails are mounted, the base 202 is configured to translate (e.g., in a rectilinear path, in a curvilinear path, or both) within a room. Furthermore, instead of two rails, in other embodiments, the base 202 may be configured to move along only one rail, or more than two rails. In still further embodiments, the rails 240, 242 may not be required. For example, in other embodiments, the base 202 may include one or more wheels for allowing the base 202 to move in a room. In some cases, the base 202 may have multiple wheels and the base 202 is steerable. Also, in some embodiments, the moveable base 202 may allow the patient supporting device to be transported outside the treatment room into a hallway and/or to another room.

In addition, in other embodiments, instead of defining the path of the base 202 using rail(s), the base 202 may include wheels and the positioning of the base 202 may be accomplished by turning and/or steering the wheels. In one implementation, the base 202 may include omni-directional wheels. In other embodiments, the base 202 may include other types of wheels, such as tractor-type wheels.

In any of the embodiments described herein, the patient supporting device 200 may also include a control for allowing an operator to enter one or more commands to control a positioning and/or a movement of the platform 230. For example, in some cases, the control may include a keyboard and/or a mouse for allowing a user to prescribe a coordinate and/or an orientation for the platform 230. In response to the command(s) entered by the operator, a processing unit may then operate the platform 230, the first member 210, the second member 220, the base 202, or any combination of the foregoing, in order to place the platform 230 at the prescribed coordinate and/or orientation. As another example, the control may include a control-stick. In such cases, in response to the operator operating the control-stick in a certain direction (e.g., left, right, forward, backward), the platform 230 will move in the corresponding direction. In some embodiments, the control-stick may also include an up-button and a down-button for moving the platform 230 upward and downward, respectively. Furthermore, in some cases, the user-operable control may be implemented using an iphone, an ipad, a tablet, a laptop, or any of other communication devices. In some embodiments, the control may be in the same room with the patient supporting device 200. In other embodiments, the control and the patient supporting device 200 may be in separate respective rooms. Also, the control may be implemented at the patient supporting device 200, and may be a part of the patient supporting device 200. Furthermore, the control may have a first control interface (e.g., keyboard, mouse, screen, touchscreen, buttons, joystick, or any combination of the foregoing) at the patient supporting device 200, and a second control interface (e.g., keyboard, mouse, screen, touchscreen, buttons, joystick, or any combination of the foregoing) in a room that is different from the room in which the platform 230 is located. In such cases, an operator may selectively choose which of the control interfaces to use for controlling the positioning and/or the movement of the platform 230.

It should be noted that as used in this specification, the term "vertical" refers to an orientation that is approximately 90° (e.g., 90°±10°, and more preferably 90°±5°) with respect to a horizon or a horizontal floor. Also, as used in this specification, the term "horizontal" refers to an orientation that is approximately parallel (e.g., at 0°±10°, and more preferably 0°±5°) to a horizon or a horizontal floor.

Figure 7:
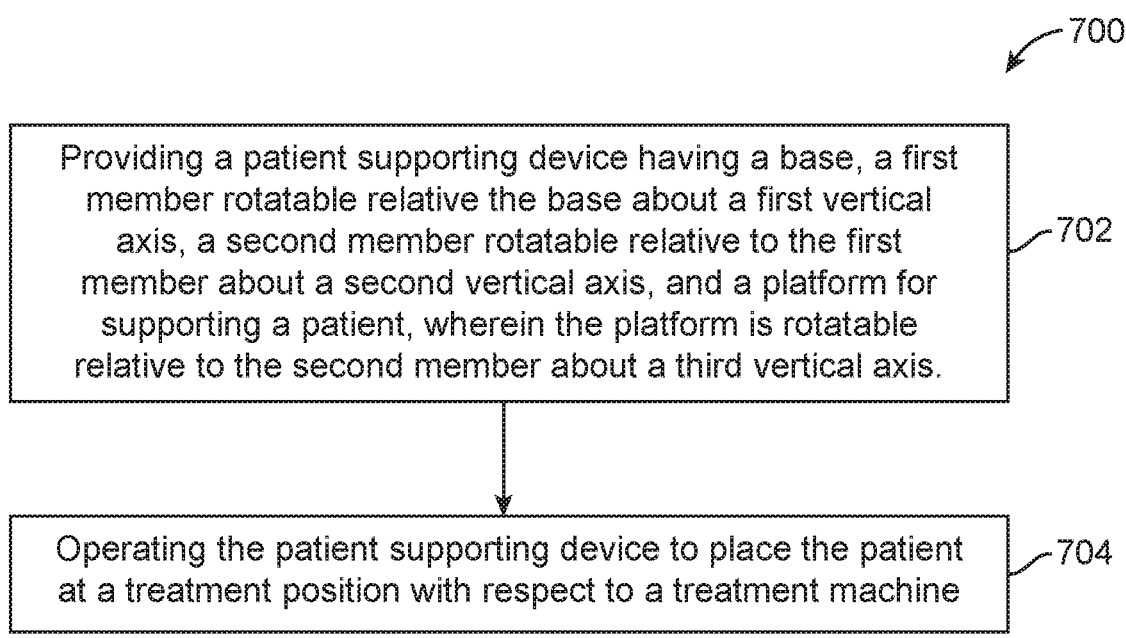
FIG. 7 illustrates a medical method in accordance with some embodiments.

FIG. 7 illustrates a medical method 700 that includes: providing a patient supporting device (item 702). In some embodiments, the patient supporting device includes a base, a first member rotatable relative the base about a first vertical axis, a second member rotatable relative to the first member about a second vertical axis, and a platform for supporting a patient, wherein the platform is rotatable relative to the second member about a third vertical axis. The method 700 also includes operating the patient supporting device to place the patient at a treatment position with respect to a treatment machine (item 704).

Optionally, the act (item 704) of operating the patient supporting device comprises rotating the platform relative to the second member about the third vertical axis.

Optionally, the act (item 704) of operating the patient supporting device also comprises rotating the second member relative to the first member about the second vertical axis.

Optionally, the act (item 704) of operating the patient supporting device also comprises rotating the first member relative to the base about the first vertical axis.

Optionally, the act (item 704) of operating the patient supporting device also comprises moving the base.

Optionally, the act (item 704) of moving the base comprises translating the base along a rectilinear path.

Optionally, the act (item 704) of operating the patient supporting device also comprises moving the platform vertically.

Optionally, the patient supporting device is operated to place a first portion of the platform under an energy output of the treatment machine, and wherein the medical method further comprises moving a second portion of the platform along a horizontal path while maintaining the first portion of the platform under the energy output.

Optionally, the second portion of the platform is moved by moving the platform relative to the second member, moving the second member relative to the first member, moving the first member relative to the base, moving the base, or any combination of the foregoing.

Optionally, act of operating the patient supporting device is performed to place the platform at an orientation with respect to the treatment machine, and wherein when the platform is at the orientation, a longitudinal axis of the platform forms an acute angle with respect to a machine axis that extends from a front of the treatment machine to a back of the treatment machine.

Optionally, the medical method 700 further includes rotating an energy output at the treatment machine while the platform is at the orientation.

Optionally, the act of rotating the energy output comprises rotating a ring gantry.

Optionally, the act of rotating the energy output comprises rotating an arm that comprises the energy output.

Optionally, medical method 700 further includes operating the patient supporting device to place the patient at an imaging position with respect to an imaging machine.

Optionally, the treatment machine and the imaging machine are in a side-by-side configuration.

Optionally, the treatment machine and the imaging machine are in a back-to-back configuration.

Optionally, the treatment machine and the imaging machine are in a front-to-front configuration.

Optionally, the imaging machine comprises a CT machine, a x-ray machine, a fluoroscope, a MRI machine, an ultrasound device, a PET machine, a SPECT machine, or a PET-CT machine.

Optionally, the medical method further includes delivering treatment radiation by the treatment machine.

Optionally, the medical method further includes delivering a proton beam by the treatment machine.

Specialized Processing System

Figure 8:
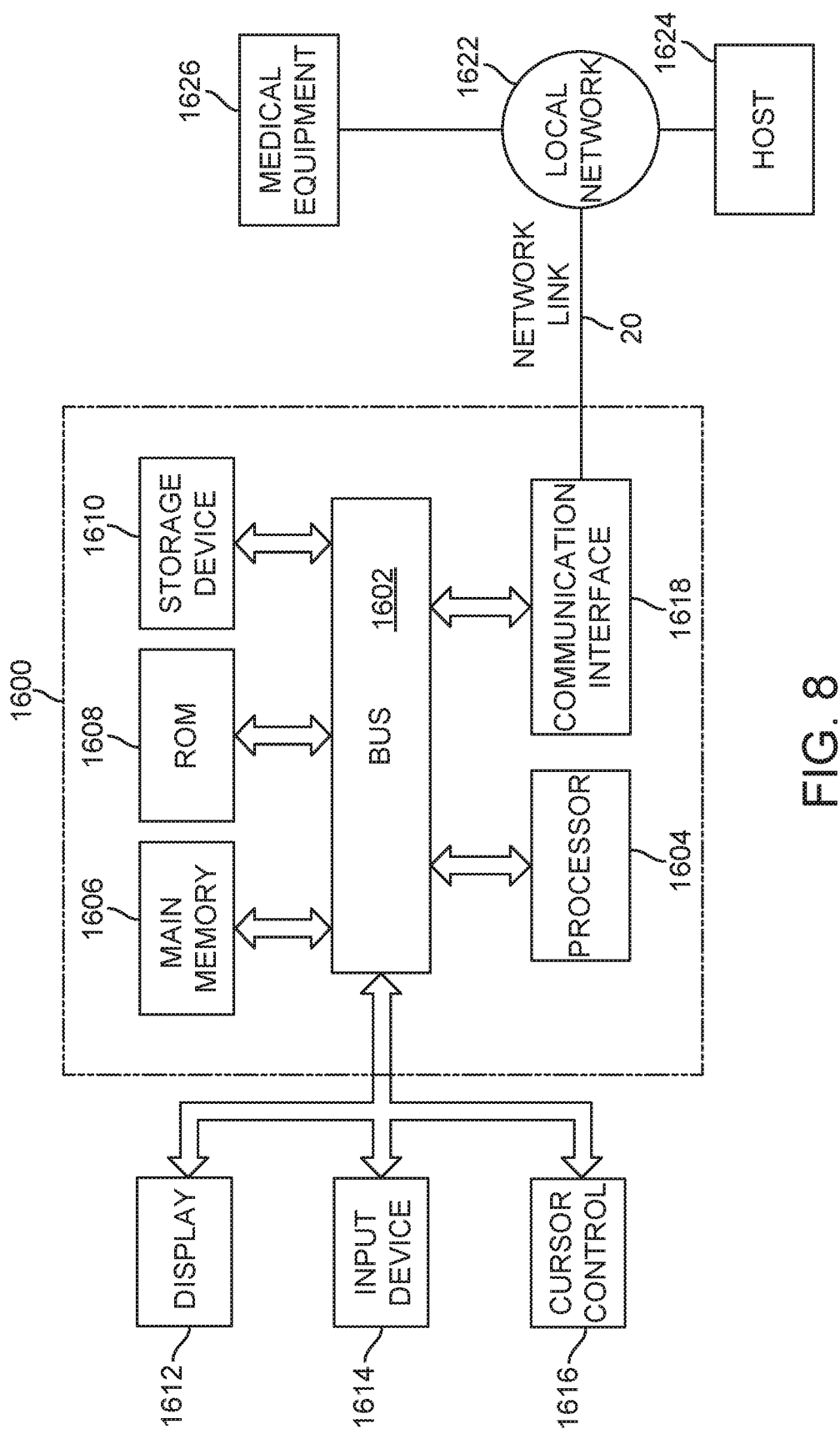
FIG. 8 is a block diagram of a specialized processing system.

FIG. 8 is a block diagram illustrating an embodiment of a specialized processing system 1600 that can be used to implement various embodiments described herein. For example, the processing system 1600 may be configured to operate the patient supporting device 200 in accordance with some embodiments. Also, in some embodiments, the processing system 1600 may be used to implement the control for the patient supporting device 200 and/or the processing unit 54 of FIG. 1. The processing system 1600 may also be an example of any processor described herein.

Processing system 1600 includes a bus 1602 or other communication mechanism for communicating information, and a processor 1604 coupled with the bus 1602 for processing information. The processor system 1600 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution of instructions to be executed by the processor 1604. The processor system 1600 further includes a read only memory (ROM) 1608 or other static storage device coupled to the bus 1602 for storing static information and instructions for the processor 1604. A data storage device 1610, such as a magnetic disk or optical disk, is provided and coupled to the bus 1602 for storing information and instructions.

The processor system 1600 may be coupled via the bus 1602 to a display 167, such as a cathode ray tube (CRT), for displaying information to a user. An input device 1614, including alphanumeric and other keys, is coupled to the bus 1602 for communicating information and command selections to processor 1604. Another type of user input device is cursor control 1616, such as a mouse, a trackball, or cursor direction keys for communicating direction information and command selections to processor 1604 and for controlling cursor movement on display 167. This input device typically has two degrees of freedom in two axes, a first axis (e.g., x) and a second axis (e.g., y), that allows the device to specify positions in a plane.

In some embodiments, the processor system 1600 can be used to perform various functions described herein. According to some embodiments, such use is provided by processor system 1600 in response to processor 1604 executing one or more sequences of one or more instructions contained in the main memory 1606. Those skilled in the art will know how to prepare such instructions based on the functions and methods described herein. Such instructions may be read into the main memory 1606 from another processor-readable medium, such as storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the various embodiments described herein. Thus, embodiments are not limited to any specific combination of hardware circuitry and software.

The term "processor-readable medium" as used herein refers to any medium that participates in providing instructions to the processor 1604 for execution. Such a medium may take many forms, including but not limited to, non-volatile media, volatile media, and transmission media. Non-volatile media includes, for example, optical or magnetic disks, such as the storage device 1610. A non-volatile medium may be considered an example of non-transitory medium. Volatile media includes dynamic memory, such as the main memory 1606. A volatile medium may be considered an example of non-transitory medium. Transmission media includes coaxial cables, copper wire and fiber optics, including the wires that comprise the bus 1602. Transmission media can also take the form of acoustic or light waves, such as those generated during radio wave and infrared data communications.

Common forms of processor-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a processor can read.

Various forms of processor-readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the processing system 1600 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received by the main memory 1606 may optionally be stored on the storage device 1610 either before or after execution by the processor 1604.

The processing system 1600 also includes a communication interface 1618 coupled to the bus 1602. The communication interface 1618 provides a two-way data communication coupling to a network link 1620 that is connected to a local network 1622. For example, the communication interface 1618 may be an integrated services digital network (ISDN) card or a modem to provide a data communication connection to a corresponding type of telephone line. As another example, the communication interface 1618 may be a local area network (LAN) card to provide a data communication connection to a compatible LAN. Wireless links may also be implemented. In any such implementation, the communication interface 1618 sends and receives electrical, electromagnetic or optical signals that carry data streams representing various types of information.

The network link 1620 typically provides data communication through one or more networks to other devices. For example, the network link 1620 may provide a connection through local network 1622 to a host computer 1624 or to equipment 1626 such as a radiation beam source or a switch operatively coupled to a radiation beam source. The data streams transported over the network link 1620 can comprise electrical, electromagnetic or optical signals. The signals through the various networks and the signals on the network link 1620 and through the communication interface 1618, which carry data to and from the processing system 1600, are exemplary forms of carrier waves transporting the information. The processing system 1600 can send messages and receive data, including program code, through the network(s), the network link 1620, and the communication interface 1618.

Although particular embodiments have been shown and described, it will be understood that they are not intended to limit the present inventions, and it will be obvious to those skilled in the art that various changes and modifications may be made without departing from the spirit and scope of the present inventions. The specification and drawings are, accordingly, to be regarded in an illustrative rather than restrictive sense. The present inventions are intended to cover alternatives, modifications, and equivalents, which may be included within the spirit and scope of the present inventions as defined by the claims.

What is claimed:

1. A patient supporting device, comprising:
    a base;
    a first member having a first end and a second end, wherein the first end of the first member is rotatably coupled to the base so that the first member is rotatable relative to the base about a first vertical axis, wherein the first member is rotatable about the first vertical axis above the base;
    a second member having a first end and a second end, wherein the first end of the second member is rotatably coupled to the second end of the first member so that the second member is rotatable relative to the first member about a second vertical axis; and
    a platform for supporting a patient, wherein the platform is rotatably coupled to the second end of the second member so that the platform is rotatable relative to the second member about a third vertical axis;
    wherein the second member comprises a first member portion and a second member portion, the first member portion comprising the first end of the second member, the second member portion comprising the second end of the second member, wherein the second member portion is rotatably coupled to the first member portion via a first connection so that the second member portion is rotatable relative to the first member portion about a first horizontal axis, wherein the first connection is located closer to the first end of the second member than to the second end of the second member; and
    wherein the platform is rotatably coupled to the second member portion so that the platform is rotatable relative to the second member portion about a second horizontal axis, the first horizontal axis and the second horizontal axis being parallel to each other, and wherein the second member portion is moveable to place the second horizontal axis at a different elevation with respect to the first horizontal axis.

2. The patient supporting device of claim 1, wherein a rotation of the platform relative to the second member portion about the second horizontal axis, and a rotation of the second member portion relative to the first member portion about the first horizontal axis, are synchronized to move the platform vertically.

3. The patient supporting device of claim 1, wherein the base is configured to move along a first rail.

4. The patient supporting device of claim 1, wherein the first member comprises a first arm, and the second member comprises a second arm.

5. The patient supporting device of claim 1, wherein the platform comprises a longitudinal axis, and the platform is configured to tilt about the longitudinal axis.

6. The patient supporting device of claim 1, further comprising one or more cameras coupled to the platform.

7. The patient supporting device of claim 6, wherein the one or more cameras comprises an optical camera, a depth camera, or both.

8. The patient supporting device of claim 1, wherein the platform is detachably coupled to a remaining part of the patient supporting device.

9. The patient supporting device of claim 8, further comprising a control for allowing an operator to enter one or more commands to control a positioning and/or movement of the platform.

10. The patient supporting device of claim 1, further comprising one or more positional indicators.

11. The patient supporting device of claim 10, wherein the one or more positional indicators comprise one or more markers at the platform, one or more markers at the first member, one or more markers at the second member, one or more markers at the base, or any combination of the foregoing.

12. The patient supporting device of claim 10, wherein the one or more positional indicators comprise one or more beacons at the platform, one or more beacons at the first member, one or more beacons at the second member, one or more beacons at the base, or any combination of the foregoing.

13. The patient supporting device of claim 10, wherein the one or more positional indicators comprise one or more components at the platform, one or more components at the first member, one or more components at the second member, one or more components at the base, or any combination of the foregoing.

14. The patient supporting device of claim 1, wherein the base is configured to translate relative to a floor, a ceiling, or a wall, along a rectilinear path, a curvilinear path, or both.

15. The patient supporting device of claim 1, wherein the base is moveably coupled to a floor.

16. The patient supporting device of claim 1, wherein the base is moveably coupled to a ceiling.

17. The patient supporting device of claim 1, wherein the base is moveably coupled to a wall.

18. A medical system comprising the patient supporting device of claim 1, and a treatment machine, wherein the patient supporting device is configured to place the patient at a treatment position with respect to the treatment machine.

19. The medical system of claim 18, wherein the patient supporting device is configured to place a first portion of the platform under an energy output of the treatment machine, and to move a second portion of the platform along a horizontal path while maintaining the first portion of the platform under the energy output.

20. The medical system of claim 19, wherein the patient supporting device is configured to move the second portion of the platform by moving the platform relative to the second member, moving the second member relative to the first member, moving the first member relative to the base, moving the base, or any combination of the foregoing.

21. The medical system of claim 18, wherein the patient supporting device is configured to place the platform at an orientation with respect to the treatment machine, and wherein when the platform is at the orientation, a longitudinal axis of the platform forms an acute angle with respect to a machine axis that extends from a front of the treatment machine to a back of the treatment machine.

22. The medical system of claim 21, wherein the treatment machine is configured to rotate an energy output while the platform is at the orientation.

23. The medical system of claim 18, further comprising an imaging machine, wherein the patient supporting device is configured to place the patient at an imaging position with respect to the imaging machine.

24. The medical system of claim 23, wherein the treatment machine and the imaging machine are in a side-by-side configuration.

25. The medical system of claim 23, wherein the treatment machine and the imaging machine are in a back-to-back configuration.

26. The medical system of claim 23, wherein the treatment machine and the imaging machine are in a front-to-front configuration.

27. The medical system of claim 23, wherein the imaging machine comprises a CT machine, a x-ray machine, a fluoroscope, a MRI machine, an ultrasound device, a PET machine, a SPECT machine, or a PET-CT machine.

28. The medical system of claim 23, wherein the patient supporting device is configured to move the platform in accordance with a first movement scheme when the platform is in a first coordinate system associated with the treatment machine, and to move the platform in accordance with a second movement scheme when the platform is in a second coordinate system associated with the imaging machine, the second movement scheme being different from the first movement scheme.

29. The medical system of claim 18, wherein the treatment machine comprises a radiation treatment machine.

30. The medical system of claim 29, wherein the radiation treatment machine comprises a ring gantry.

31. The medical system of claim 29, wherein the radiation treatment machine comprises an arm having an energy output and a collimator.

32. The medical system of claim 18, wherein the treatment machine comprises a proton treatment machine.

33. The patient supporting device of claim 1, wherein the first end of the first member is rotatably coupled to the base via a second connection having a fixed elevation, and wherein the second connection allows the first member to rotate relative to the base about the first vertical axis by more than 180°, and wherein the second end of the first member is rotatably coupled to the first end of the second member via a third connection that allows the second member to rotate relative to the first member about the second vertical axis.

34. A medical method, comprising:
providing a patient supporting device having a base, a first member rotatable relative the base about a first vertical axis, a second member rotatable relative to the first member about a second vertical axis, and a platform for supporting a patient, wherein the platform is rotatable relative to the second member about a third vertical axis, wherein the first member is rotatable about the first vertical axis above the base; and
operating the patient supporting device to place the patient at a treatment position with respect to a treatment machine;
wherein the second member comprises a first member portion and a second member portion, the first member portion comprising a first end of the second member, the second member portion comprising a second end of the second member, and wherein the method further comprises rotating the second member portion relative to the first member portion about a first horizontal axis, wherein the first member portion and the second member portion are rotatably coupled to each other via a first connection, and wherein the first connection is closer to the first end of the second member than to the second end of the second member; and
wherein the platform is rotatably coupled to the second member portion, and wherein the method further comprises rotating the platform relative to the second member portion about a second horizontal axis, the first horizontal axis and the second horizontal axis being parallel to each other, and wherein the second member portion is moveable to place the second horizontal axis at a different elevation with respect to the first horizontal axis.

35. The medical method of claim 34, wherein the act of operating the patient supporting device comprises rotating the platform relative to the second member about the third vertical axis.

36. The medical method of claim 35, wherein the act of operating the patient supporting device also comprises rotating the second member relative to the first member about the second vertical axis.

37. The medical method of claim 35, wherein the act of operating the patient supporting device also comprises rotating the first member relative to the base about the first vertical axis.

38. The medical method of claim 35, wherein the act of operating the patient supporting device also comprises moving the platform vertically.

39. The medical method of claim 34, wherein the act of operating the patient supporting device comprises translating the base along a rectilinear path.

40. The medical method of claim 34, wherein the act of operating the patient supporting device comprises translating the base along a curvilinear path.

41. The medical method of claim 34, wherein the patient supporting device is operated to place a first portion of the platform under an energy output of the treatment machine, and wherein the medical method further comprises moving a second portion of the platform along a horizontal path while maintaining the first portion of the platform under the energy output.

42. The medical method of claim 41, wherein the second portion of the platform is moved by moving the platform relative to the second member, moving the second member relative to the first member, moving the first member relative to the base, moving the base, or any combination of the foregoing.

43. The medical method of claim 34, wherein the act of operating the patient supporting device is performed to place the platform at an orientation with respect to the treatment machine, and wherein when the platform is at the orientation, a longitudinal axis of the platform forms an acute angle with respect to a machine axis that extends from a front of the treatment machine to a back of the treatment machine.

44. The medical method of claim 43, further comprising rotating an energy output at the treatment machine while the platform is at the orientation.

45. The medical method of claim 44, wherein the act of rotating the energy output comprises rotating a ring gantry.

46. The medical method of claim 44, wherein the act of rotating the energy output comprises rotating an arm that comprises the energy output.

47. The medical method of claim 34, further comprising operating the patient supporting device to place the patient at an imaging position with respect to an imaging machine.

48. The medical method of claim 47, wherein the treatment machine and the imaging machine are in a side-by-side configuration.

49. The medical method of claim 47, wherein the treatment machine and the imaging machine are in a back-to-back configuration.

50. The medical method of claim 47, wherein the treatment machine and the imaging machine are in a front-to-front configuration.

51. The medical method of claim 47, wherein the imaging machine comprises a CT machine, a x-ray machine, a fluoroscope, a MRI machine, an ultrasound device, a PET machine, a SPECT machine, or a PET-CT machine.

52. The medical method of claim 47, further comprising:
operating the patient supporting device to move the platform in accordance with a first movement scheme when the platform is in a first coordinate system associated with the treatment machine; and
operating the patient supporting device to move the platform in accordance with a second movement scheme when the platform is in a second coordinate system associated with the imaging machine, the second movement scheme being different from the first movement scheme.

53. The medical method of claim 34, further comprising delivering treatment radiation by the treatment machine.

54. The medical method of claim 34, further comprising delivering a proton beam by the treatment machine.

55. The method of claim 34, wherein a first end of the first member is rotatably coupled to the base via a second connection having a fixed elevation, and wherein the first second connection allows the first member to rotate relative to the base about the first vertical axis by more than 180°, and wherein a second end of the first member is rotatably coupled to the second member via a third connection that allows the second member to rotate relative to the first member about the second vertical axis.

* * * * *